United States Patent [19]

Ward

[11] 4,141,984
[45] Feb. 27, 1979

[54] N-(1,3,4-THIADIAZOL-2-YL)BENZAMIDES

[75] Inventor: John S. Ward, Indianapolis, Ind.

[73] Assignee: Eli Lilly and Company, Indianapolis, Ind.

[21] Appl. No.: 824,687

[22] Filed: Aug. 15, 1977

Related U.S. Application Data

[63] Continuation-in-part of Ser. No. 740,166, Nov. 10, 1976, abandoned, which is a continuation-in-part of Ser. No. 656,552, Feb. 9, 1976, abandoned.

[51] Int. Cl.$^2$ .................... A01N 9/12; C07D 285/12; C07D 417/04
[52] U.S. Cl. ............................... 424/270; 260/304 R; 260/305; 260/330.5; 260/552 SC; 424/258; 424/263; 542/418; 546/277; 546/167
[58] Field of Search ................ 260/306.8 D; 424/270

[56] References Cited

U.S. PATENT DOCUMENTS 3,728,354  4/1973  Rucker et al. ............... 260/306.8 D

OTHER PUBLICATIONS

Hoggarth, J. Chem. Soc. (London), 1949, pp. 1163–1167.

*Primary Examiner*—Alton D. Rollins
*Attorney, Agent, or Firm*—Leroy Whitaker; Arthur R. Whale

[57] ABSTRACT

A series of N-(1,3,4-thiadiazol-2-yl)benzamides, having a phenyl, naphthyl or hetero-aryl group at the 5-position of the thiadiazole ring and 2,6-substitution on the benzamide ring, are useful insecticides. The invention also provides insecticidal methods and compositions.

62 Claims, No Drawings

N-(1,3,4-THIADIAZOL-2-YL)BENZAMIDES

CROSS-REFERENCE

This application is a continuation-in-part of my copending application Ser. No. 740,166, filed Nov. 10, 1976, now abandoned which in turn is a continuation-in-part of my then copending application Ser. No. 656,552, filed Feb. 9, 1976, now abandoned.

BACKGROUND OF THE INVENTION

The control of insects was one of the first problems undertaken by agricultural chemical research, and continues to be pursued vigorously by the art. Insects of many orders assault crops of all types, and also cause unsanitary conditions and nuisance by contaminating foodstuffs. The damage caused by insects is incalculable, and the control of harmful insects necessarily is of the highest priority.

Recently, the search for new and better insecticides has been spurred by the withdrawal from use of the old residual insecticides.

The compounds of this invention are new to organic chemistry. Some items in the prior art, however, are of interest. For example, Cebalo, U.S. Patent 3,726,892, discloses herbicidal 1,3,4-thiadiazol-2-ylureas.

Rao, *Indian J. Chem.* 8, 509-13 (1970), teaches a synthesis method for 2-amino-1,3,4-thiadiazoles, which are intermediates for the compounds of this invention.

Wellinga and Mulder, U.S. Pat. No. 3,748,356, show herbicidal and insecticidal efficacy of N-benzoyl-N'-phenylureas.

SUMMARY OF THE INVENTION

This invention belongs to the field of agricultural chemistry, and provides new insecticides of the formula

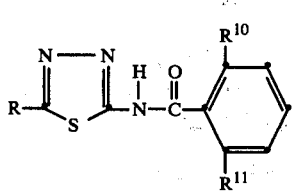

(I)

wherein R represents

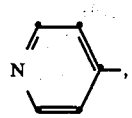

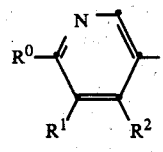

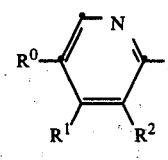

-continued

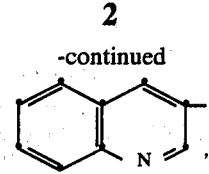

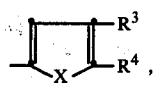

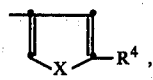

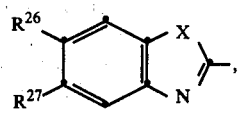

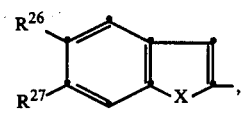

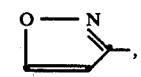

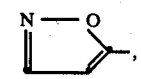

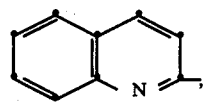

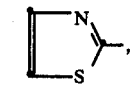

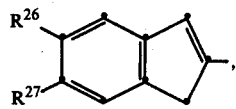

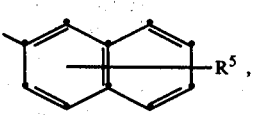

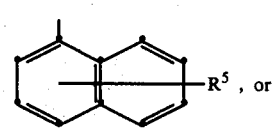

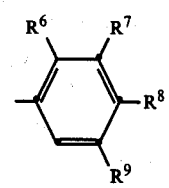

wherein
$R^0$, $R^1$ and $R^2$ independently represent hydrogen, chloro or bromo, provided that at least one of $R^0$, $R^1$ and $R^2$ represents chloro or bromo;
X represents oxygen or sulfur;

$R^3$ and $R^4$ independently represent hydrogen, chloro, bromo or methyl, provided that $R^3$ represents hydrogen when X represents oxygen;

$R^5$ represents hydrogen, chloro, bromo, fluoro or trifluoromethyl;

one of $R^{26}$ and $R^{27}$ represents hydrogen and the other of $R^{26}$ and $R^{27}$ represents hydrogen, fluoro, chloro, bromo, trifluoromethyl or methoxy;

and either
  (1) $R^6$ and $R^7$ represent hydrogen, one of $R^8$ and $R^9$ represents hydrogen, and the other of $R^8$ and $R^9$ represents hydrogen, acetamido, chloro, methoxy, bromo, iodo, fluoro, trifluoromethyl, methyl, hydroxy, phenyl, or phenyl monosubstituted with bromo, chloro or fluoro, or
  (2) $R^6$ and $R^7$ represent hydrogen, and $R^8$ and $R^9$ independently represent chloro, fluoro or bromo, or
  (3) $R^6$ and $R^8$ represent hydrogen, and $R^7$ and $R^9$ independently represent chloro, fluoro, bromo or trifluoromethyl, or
  (4) $R^7$ and $R^9$ represent hydrogen, and $R^6$ and $R^8$ independently represent chloro, fluoro or bromo, or
  (5) $R^7$, $R^8$ and $R^9$ represent hydrogen, and $R^6$ represents chloro, fluoro or bromo, or
  (6) $R^6$, $R^7$ and $R^9$ represent hydrogen, and $R^8$ represents nitro, amino or cyano, or
  (7) $R^6$ and $R^7$ represent hydrogen, one of $R^8$ and $R^9$ represents hydrogen and the other of $R^8$ and $R^9$ represents $C_1$-$C_2$ alkoxy substituted with one or more fluorine atoms;

$R^{10}$ and $R^{11}$ independently represent hydrogen, chloro, fluoro, bromo, methyl or methoxy; provided that:
  (1) one of $R^{10}$ and $R^{11}$ may represent hydrogen, if and only if the other represents methoxy;
  (2) at least one of $R^{10}$ and $R^{11}$ must represent methyl or methoxy, unless
    a) $R^8$ does not represent hydrogen, and $R^6$, $R^7$ and $R^9$ represent hydrogen, or
    b) $R^6$ and $R^8$ represent hydrogen, and one or both of $R^7$ and $R^9$ represent trifluoromethyl;
  (3) neither $R^8$ nor $R^9$ represents phenyl, acetamido, methoxy, nitro, amino, cyano or substituted phenyl unless both $R^{10}$ and $R^{11}$ represent methoxy;
  (4) two of $R^7$, $R^8$ and $R^9$ represent hydrogen unless both $R^{10}$ and $R^{11}$ represent methyl or methoxy;
  (5) both $R^{10}$ and $R^{11}$ represent methoxy or methyl when R represents pyridyl, naphthyl, furyl or thienyl;
  (6) both $R^{10}$ and $R^{11}$ represent methoxy when R represents benzothiazolyl, benzoxazolyl, benzothienyl, benzofuryl, isoxazolyl, quinolyl or thiazolyl.

Insecticidal methods and insecticidal compositions making use of the compounds are also provided.

DESCRIPTION OF THE PREFERRED EMBODIMENT

Throughout this document, all quantities are measured in the metric system, and temperatures are on the Celsius scale. All proportions and percentages are by weight. The term halogen refers to fluoro, chloro, bromo and iodo.

A number of specific classes and types of compounds of this invention constitute preferred classes. A particularly preferred class of compounds are those which are of the formula

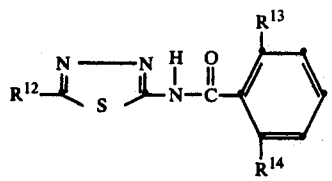 (II)

wherein $R^{12}$ represents

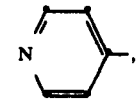

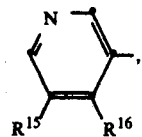

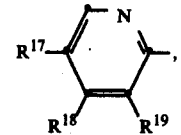

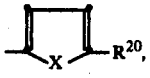

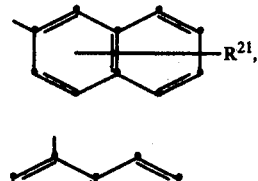

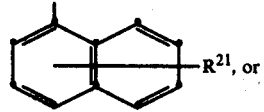

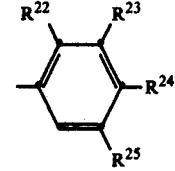

wherein
$R^{15}$, $R^{16}$, $R^{17}$, $R^{18}$ and $R^{19}$ independently represent hydrogen, chloro or bromo, provided that at least one of $R^{15}$ and $R^{16}$, or at least one of $R^{17}$, $R^{18}$ and $R^{19}$ represents chloro or bromo;
X represents oxygen or sulfur;
$R^{20}$ represents hydrogen, chloro, bromo or methyl;
$R^{21}$ represents hydrogen, chloro, bromo, fluoro or trifluoromethyl;
and either
  (1) $R^{22}$ and $R^{23}$ represent hydrogen, one of $R^{24}$ and $R^{25}$ represents hydrogen, and the other of $R^{24}$ and $R^{25}$ represents hydrogen, chloro, bromo, fluoro, trifluoromethyl, methyl, hydroxy, phenyl, or phenyl monosubstituted with bromo, chloro or fluoro, or
(2) $R^{22}$ and $R^{23}$ represent hydrogen, and $R^{24}$ and $R^{25}$ independently represent chloro, fluoro or bromo, or
(3) $R^{22}$ and $R^{24}$ represent hydrogen, and $R^{23}$ and $R^{25}$ independently represent chloro, fluoro, bromo or trifluoromethyl, or
(4) $R^{23}$ and $R^{25}$ represent hydrogen, and $R^{22}$ and $R^{24}$ independently represent chloro, fluoro or bromo, or
(5) $R^{23}$, $R^{24}$ and $R^{25}$ represent hydrogen, and $R^{22}$ represents chloro, fluoro or bromo, or
(6) $R^{22}$ and $R^{23}$ represent hydrogen, one of $R^{24}$ and $R^{25}$ represents hydrogen and the other of $R^{24}$ and $R^{25}$ represents $C_1$-$C_2$ alkoxy substituted with one or more fluorine atoms;
$R^{13}$ and $R^{14}$ independently represent hydrogen, chloro, fluoro, bromo, methyl or methoxy; provided that:
(1) one of $R^{13}$ and $R^{14}$ may represent hydrogen, if and only if the other represents methoxy;
(2) at least one of $R^{13}$ and $R^{14}$ must represent methyl or methoxy, unless
  a) $R^{24}$ does not represent hydrogen, and $R^{22}$, $R^{23}$ and $R^{25}$ represent hydrogen, or
  b) $R^{22}$ and $R^{24}$ represent hydrogen, and one or both of $R^{23}$ and $R^{25}$ represent trifluoromethyl;
(3) neither $R^{24}$ nor $R^{25}$ represents phenyl or substituted phenyl unless both $R^{13}$ and $R^{14}$ represent methoxy;
(4) two of $R^{23}$, $R^{24}$ and $R^{25}$ represent hydrogen unless both $R^{13}$ and $R^{14}$ represent methyl or methoxy;
(5) both $R^{13}$ and $R^{14}$ represent methoxy when $R^{12}$ represents pyridyl, naphthyl, furyl or thienyl.

Within the above class, a more preferred class includes the compound wherein $R^{12}$ represents

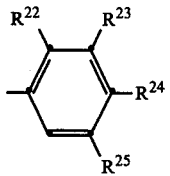

and a further preferred class includes the compounds wherein both $R^{13}$ and $R^{14}$ represent methoxy.

Another particularly preferred class of compounds are those of formula II wherein $R^{12}$ represents

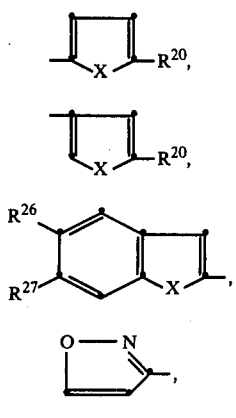

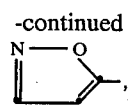

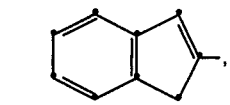

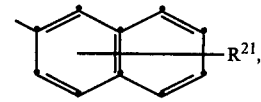

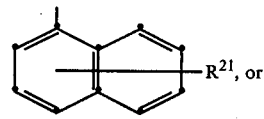

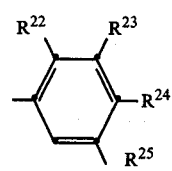

and all the other groups have the meanings assigned above.

It will be understood that the present invention also includes a number of other different types or classes of compounds, and also includes insecticidal methods and compositions making use of the various classes of compounds. For example, the following preferred classes of compounds are contemplated. Each numbered subparagraph below describes an independent class of compounds; in each class, the variable substituents have the general meanings in the general formula in the Summary section of this document, if not otherwise stated. In the subparagraphs below, each general term, such as phenyl, is intended to include the substituted forms of the group referred to.

Compounds wherein:

(1) R represents phenyl;
(2) R represents phenyl, or pyridyl;
(3) R represents pyridyl, thienyl, furyl, benzothienyl, benzofuryl, benzothiazolyl, benzoxazolyl, isoxazolyl, quinolyl or thiazolyl;
(4) R represents phenyl or naphthyl;
(5) R represents pyridyl, benzothiazolyl, benzoxazolyl, isoxazolyl, quinolyl or thiazolyl;
(6) R represents thienyl, furyl, benzoxazolyl, benzothiazolyl, benzothienyl, benzofuryl, isoxazolyl, quinolyl or thiazolyl;
(7) one of $R^8$ and $R^9$ represents hydrogen, and the other represents halogen or trifluoromethyl;
(8) $R^8$ and $R^9$ independently represent chloro, fluoro or bromo;
(9) $R^7$ and $R^9$ independently represent chloro, fluoro, bromo or trifluoromethyl;
(10) one of $R^8$ and $R^9$ represents hydrogen, and the other represents halogen, trifluoromethyl, methyl or methoxy;
(11) $R^{10}$ and $R^{11}$ represent methoxy;
(12) $R^{10}$ and $R^{11}$ independently represent methyl or methoxy;

(13) $R^{10}$ and $R^{11}$ independently represent chloro, fluoro or bromo;

Compounds of subparagraph 11 above wherein:

(14) R represents phenyl;
(15) R represents phenyl or pyridyl;
(16) R represents pyridyl, thienyl, furyl, benzothienyl, benzofuryl, benzothiazolyl, benzoxazolyl, isoxazolyl, quinolyl or thiazolyl;
(17) R represents phenyl or naphthyl;
(18) R represents pyridyl, benzothiazolyl, benzoxazolyl, isoxazolyl, quinolyl or thiazolyl;
(19) R represents thienyl, furyl, benxoxazolyl, benzothiazolyl, benzothienyl, benzofuryl, isoxazolyl, quinolyl or thiazolyl;
(20) One of $R^8$ and $R^9$ represents hydrogen, and the other represents halogen or trifluoromethyl;
(21) $R^8$ and $R^9$ independently represent chloro, fluoro or bromo;
(22) $R^7$ and $R^9$ independently represent chloro, fluoro, bromo or trifluoromethyl;
(23) one of $R^8$ and $R^9$ represents hydrogen, and the other represents halogen, trifluoromethyl, methyl or methoxy;

Compounds of subparagraph 12 above wherein;

(24) R represents phenyl;
(25) R represents phenyl or pyridyl;
(26) R represents pyridyl, thienyl, furyl, benzothienyl, benzofuryl, benzothiazolyl, benzoxazolyl, isoxazolyl, quinolyl or thiazolyl;
(27) R represents phenyl or naphthyl;
(28) R represents pyridyl, benzothiazolyl, benzoxazolyl, isoxazolyl, quinolyl or thiazolyl;
(29) R represents thienyl, furyl, benzoxazolyl, benzothiazolyl, benzothienyl, benzofuryl, isoxazolyl, quinolyl or thiazolyl;
(30) One of $R^8$ and $R^9$ represents hydrogen, and the other repesents halogen or trifluoromethyl;
(31) $R^8$ and $R^9$ independently reprsent chloro, fluoro or bromo;
(32) $R^7$ and $R^9$ independently represent chloro, fluoro, bromo or trifluoromethyl;
(33) one of $R^8$ and $R^9$ represents hydrogen, and the other represents halogen, trifluoromethyl, methyl or methoxy;

Compounds of subparagraph 13 above wherein:

(34) R represents phenyl;
(35) R represents phenyl or pyridyl;
(36) R represents pyridyl, thienyl, furyl, benzothienyl, benzofuryl, benzothiazolyl, benzoxazolyl, isoxazolyl, quinolyl or thiazolyl;
(37) R represents phenyl or naphthyl;
(38) R represents pyridyl, benzothiazolyl, benzoxazolyl, isoxazolyl, quinolyl or thiazolyl;
(39) R represents thienyl, furyl, benzoxazolyl, benzothiazolyl, benzothienyl, benzofuryl, isoxazolyl, quinolyl or thiazolyl;
(40) One of $R^8$ and $R^9$ represents hydrogen, and the other represents halogen or trifluoromethyl;
(41) $R^8$ and $R^9$ independently represent chloro, fluoro or bromo;
(42) $R^7$ and $R^9$ independently represent chloro, fluoro, bromo or trifluoromethyl;
(43) one of $R^8$ and $R^9$ represents hydrogen, and the other represents halogen, trifluoromethyl, methyl or methoxy.

Although the above general formula clearly describes the compounds of this invention, the following typical examples are presented to assure that agricultural chemists fully understand the invention.

N-[5-(6-chloro-3-pyridyl)-1,3,4-thiadiazol-2-yl]-2,6-dimethoxybenzamide
N-[5-(4-chloro-3-pyridyl)-1,3,4-thiadiazol-2-yl]-2,6-dimethoxybenzamide
N-[5-(4,5-dibromo-3-pyridyl)-1,3,4-thiadiazol-2-yl]-2,6-dimethylbenzamide
N-[5-(5-bromo-2-pyridyl)-1,3,4-thiadiazol-2-yl]-2,6-dimethoxybenzamide
N-[5-(4-chloro-2-pyridyl)-1,3,4-thiadiazol-2-yl]-2,6-dimethylbenzamide
N-[5-(5-bromo-3-chloro-2-pyridyl)-1,3,4-thiadiazol-2-yl]-2,6-dimethoxybenzamide
N-[5-(3,4,5-trichloro-2-pyridyl)-1,3,4-thiadiazol-2-yl]-2,6-dimethoxybenzamide
N-[5-(3-furyl)-1,3,4-thiadiazol-2-yl]-2,6-dimethoxybenzamide
N-[5-(5-chloro-2-furyl)-1,3,4-thiadiazol-2-yl]2,6-dimethoxybenzamide
N-[5(5-bromo-3-thienyl)-1,3,4-thiadiazol-2-yl]2,6-dimethoxybenzamide
N-[5-(5-methyl-2-thienyl)-1,3,4-thiadiazol-2-yl]-2,6-dimethoxybenzamide
N-[5-(3-chloro-1-naphthyl)-1,3,4-thiadiazol-2-yl]-2,6-dimethoxybenzamide
N-[5(2-bromo-1-naphthyl)-1,3,4-thiadiazol-2-yl]-2,6-dimethoxybenzamide
N-]5-(4-fluoro-2-naphthyl)-1,3,4-thiadiazol-2-yl]-2,6-dimethoxybenzamide
N-[5-(3-trifluoromethyl-2-naphthyl)-1,3,4-thiadiazol-2-yl]-2,6-dimethoxybenzamide
N-[5-(4-chlorophenyl)-1,3,4-thiadiazol-2-yl]-2-bromo-6-fluorobenzamide
N-[5-(3-bromophenyl)-1,3,4-thiadiazol-2-yl]-2-fluoro-6-methylbenzamide
N-[5-(3-iodophenyl)-1,3,4-thiadiazol-2-yl]-2-fluoro-6-methoxybenzamide
N-[5-(3-methylphenyl)-1,3,4-thiadiazol-2-yl]-2-chloro-6-methylbenzamide
N-[5-(3-hydroxyphenyl)-1,3,4-thiadiazol-2-yl]-2-bromo-6-methylbenzamide
N-[5-(3-phenylphenyl)-1,3,4-thiadiazol-2-yl]-2,6-dimethoxybenzamide
N-[5-[3-(3-fluorophenyl)phenyl]-1,3,4-thiadiazol-2-yl]-2,6-dimethoxybenzamide
N-[5-[4-(3-bromophenyl)phenyl]-1,3,4-thiadiazol-2-yl]-2,6-dimethoxybenzamide
N-[5-[4-(2-chlorophenyl)phenyl]-1,3,4-thiadiazol-2-yl]-2,6-dimethoxybenzamide
N-5-[3-(4-chlorophenyl)phenyl]-1,3,4-thiadiazol-2-yl]-2,6-dimethoxybenzamide
N-[5-(3,4-dibromophenyl)-1,3,4-thiadiazol-2-yl]-2,6-dimethylbenzamide
N-[5-(3-bromo-4-fluorophenyl)-1,3,4-thiadiazol-2-yl]-2-methoxy-6-methylbenzamide
N-[5-(3,4-difluorophenyl)-1,3,4-thiadiazol-2-yl]-2,6-dimethoxybenzamide
N-[5-(3,5-difluorophenyl)-1,3,4-thiadiazol-2-yl]-2,6-dimethylbenzamide
N-[5-(3,5-dibromophenyl)-1,3,4-thiadiazol-2-yl]-2,6-dimethoxybenzamide
N-[5-(3-chloro-5-trifluoromethylphenyl)-1,3,4-thiadiazol-2-yl]-2,6-dimethoxybenzamide N-[5-(3-bromo-5-fluorophenyl)-1,3,4-thiadiazol-2-yl]-2-methoxy-6-methylbenzamide
N-[5-(2,4-dibromophenyl)-1,3,4-thiadiazol-2-yl]-2,6-dimethylbenzamide
N-[5-(4-fluorophenyl)-1,3,4-thiadiazol-2-yl]-2,6-difluorobenzamide
N-[5-(2-bromo-4-fluorophenyl)-1,3,4-thiadiazol-2-yl]-2,6-dimethoxybenzamide
N-[5-(4-bromo-2-chlorophenyl)-1,3,4-thiadiazol-2-yl]-2-methoxybenzamide
N-[5-(4-trifluoromethylphenyl)-1,3,4-thiadiazol-2-yl]-2,6-dichlorobenzamide
N-[5-(2-bromophenyl)-1,3,4-thiadiazol-2-yl]-methoxy-6-methylbenzamide
N-[5-(6-chloro-1-naphthyl)-1,3,4-thiadiazol-2yl]-2,6-dimethoxybenzamide
N-[5-(5-fluoro-2-naphthyl)-1,3,4-thiadiazol-2-yl)]-2,6-dimethoxybenzamide
N-[5-(7-trifluoromethyl-1-naphthyl)-1,3,4-thiadiazol-2-yl]-2,6-dimethoxybenzamide
N-[5-(4,5,6-trichloro-3-pyridyl)-1,3,4-thiadiazol-2-yl]-2,6-dimethoxybenzamide
N-[5-bromo-4,6-dichloro-3-pyridyl)-1,3,4-thiadiazol-2-yl]-2,6-dimethylbenzamide
N-[5-(3,4,5-tribromo-2-pyridyl)-1,3,4-thiadiazol-2-yl]-2-methoxy-6-methylbenzamide
N-[5-(3-bromo-4,6-dichloro-2-pyridyl)-1,3,4-thiadiazol-2-yl]-2,6-dimethoxybenzamide
N-[5-(4-methyl-2-thienyl)-1,3,4-thiadiazol-2-yl]-2,6-dimethylbenzamide
N-[5-(4-bromo-5-methyl-2-thienyl)-1,3,4-thiadiazol-2-yl]-2-methoxy-6-methylbenzamide
N-[5-(4,5-dichloro-2-thienyl)-1,3,4-thiadiazol-2-yl]-2,6-dimethoxybenzamide
N-[5-(2-benzoxazolyl)-1,3,4-thiadiazol-2-yl]-2,6-dimethoxybenzamide
N-[5-(2-benzo[b]thienyl)-1,3,4-thiadiazol-2-yl]-2,6-dimethoxybenzamide
N-[5-(2-benzo[b]furyl)-1,3,4-thiadiazol-2-yl]-2,6-dimethoxybenzamide
N-[5-(5-isoxazolyl)-1,3,4-thiadiazol-2-yl]-2,6-dimethoxybenzamide
N-[5-(2-thiazolyl)-1,3,4-thiadiazol-2-yl]-2,6-dimethoxybenzamide
N-[5-(4-iodophenyl)-1,3,4-thiadiazol-2-yl]-2-chloro-6-methoxybenzamide
N-[5-(4-iodophenyl)-1,3,4-thiadiazol-2-yl]-2,6-dichlorobenzamide
N-[5-(3-iodophenyl)-1,3,4-thiadiazol-2-yl]-2-bromo-6-methylbenzamide
N-[5-(5-trifluoromethyl-2-naphthyl)-1,3,4-thiadiazol-2-yl]-2,6-dimethylbenzamide
N-[5-(4-chloro-1-naphthyl)-1,3,4-thiadiazol-2-yl]-2-methoxy-6-methylbenzamide
N-[5-(2-furyl)-1,3,4-thiadiazol-2-yl]-2,6-dimethylbenzamide
N-[5-(5-bromo-3-furyl)-1,3,4-thiadiazol-2-yl]-2-methoxy-6-methylbenzamide
N-[5-(6-bromo-2-benzo[b]thienyl)-1,3,4-thiadiazo-2-yl]-2,6-dimethoxybenzamide
N-[5-(5-chloro-2-benzo[b]furyl)-1,3,4-thiadiazol-2-yl]-2,6-dimethoxybenzamide
N-[5-(6-fluoro-2-benzo[b]thienyl)-1,3,4-thiadiazol-2-yl]-2,6-dimethoxybenzamide
N-[5-(5-trifluoromethyl-2-benzo[b]thienyl)-1,3,4-thiadiazol-2-yl]-2,6-dimethoxybenzamide
N-[5-(5-methoxy-2-benzo[b]thienyl)-1,3,4-thiadiazol-2-yl]-2,6-dichlorobenzamide
N-[5-(5-methoxy-2-benzo[b]furyl)-1,3,4-thiadiazol-2-yl]-2,6-dichlorobenzamide
N-[5-(6-fluoro-2-benzo[b]furyl)-1,3,4-thiadiazol-2-yl]-2,6-dimethoxybenzamide
N-[5-(5-trifluoromethyl-2-benzo[b]furyl-1,3,4-thiadiazol-2-yl]-2,6-dimethoxybenzamide
N-[5-(6-methoxy-2-benzo[b]furyl)-1,3,4-thiadiazol-2-yl]-2,6-dimethoxybenzamide
N-[5-(2-indenyl)-1,3,4-thiadiazol-2-yl]-2,6-dimethoxybenzamide
N-[5-(5-chloro-2-indenyl)-1,3,4-thiadiazol-2-yl]-2,6-dichlorobenzamide
N-[5-(6-trifluoromethyl-2-indenyl)-1,3,4-thiadiazol-2-yl]-2,6-dimethoxybenzamide
N-[5-(4-pentafuoroethoxyphenyl)-1,3,4-thiadiazol-2-yl]-2,6-dimethoxybenzamide
N-[5-(3-trifluoromethoxyphenyl)-1,3,4-thiadiazol-2-yl]-2,6-dichlorobenzamide
N-[5-(4-(1,1,2,2-tetrafluoroethoxy)phenyl)-1,3,4-thiadiazol-2-yl]-2,6-dichlorobenzamide
N-[5-(4-difluoromethoxyphenyl)-1,3,4-thiadizol-2-yl]-2,6-dimethoxybenzamide
N-[5-(3-fluoromethoxyphenyl)-1,3,4-thiadiazol-2-yl]-2,6-dimethoxybenzamide The preferred compounds of this invention are N-[5-(4-chlorophenyl)-1,3,4-thiadiazol-2-yl]-2,6-dimethylbenzamide, N-[5-(4-chlorophenyl)-1,3,4-thiadiazol-2-yl]-2,6-dimethoxybenzamide, N-[5-(4-fluorophenyl)-1,3,4-thiadiazol-2-yl]-2,6-dimethylbenzamide, N-[5-(4-trifluoromethylphenyl)-1,3,4-thiadiazol-2-yl]-2,6-dimethylbenzamide, N-[5-(4-fluorophenyl)-1,3,4-thiadiazol-2-yl]-2,6-dimethoxybenzamide, N-[5-(3-trifluoromethylphenyl)-1,3,4-thiadiazol-2-yl]-2,6-dimethoxybenzamide, N-[5-(2-benxo[b]furyl)-1,3,4-thiadiazol-2-yl]-2,6-dimethoxybenzamide, N-[5-(3-chlorophenyl)-1,3,4-thiadiazol-2-yl]-2,6-dimethoxybenzamide, N-[5-(3,5-bis-(trifluoromethyl)phenyl]-1,3,4-thiadiazol-2-yl]-2,6-dimethoxybenzamide, N-[5-(4-trifluoromethylphenyl)-1,3,4-thiadiazol-2-yl]-2,6-dimethoxybenzamide, N-[5-(5-fluoro-2-benzo[b]furyl)-1,3,4-thiadiazol-2-yl]-2,6-dimethoxybenzamide, N-[5-(5-chloro-2-benzo]b]furyl)-1,3,4-thiadiazol-2-yl]-2,6-dimethoxybenzamide and N-[5-(4-pentfluorethoxyphenyl)-1,3,4-thiadiazol-2-yl]-2,6-dimethoxybenzamide.

The compounds of this invention are made by processes which are presently known or are analogous to presently-known processes. All of the compounds are readily made by the acylation of 2-amino-5-R-substituted 1,3,4-thiadiazoles of the formula

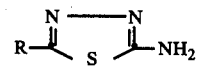

with appropriately substituted benzoyl halides of the formula

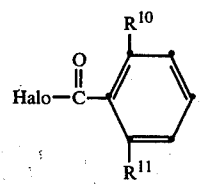

Halo in the above structure refers to chloro or bromo.

The acylation step is carried out in the presence of a base in a reaction solvent such as tetrahydrofuran, dimethylformamide, dimethylsulfoxide, diethyl ether and the like. The preferred base is sodium hydride, although organic bases such as pyridine, triethylamine and triethanolamine may be used, as can inorganic bases including sodium hydroxide, potassium carbonate and lithium bicarbonate. The temperature range of the reaction is from about −10° to about 50°, preferably from about 0° to about 25°.

The intermediate aminothidiazoles are prepared by reactions which are now well known. In general, they are prepared either by oxidative cyclization of a thiosemicarbazone, preferably with ferric chloride, or by dehydrative cyclization of a thiosemicarbazide with a strong acid. See, for example, Rao, supra, and Cebalo, supra.

All of the compounds are also conveniently prepared by a cyclization process which makes the desired products in one step. In one embodiment of the process, a 1-R-carbonyl-4-benzoylthiosemicarbazide of the formula

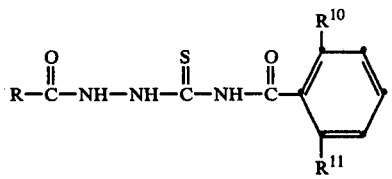

is cyclized with a dehydrating agent. Useful dehydrating agents include phosphoric acid, formic acid, phosphorus pentachloride, phosphorus pentoxide in the presence of a strong acid, and benzoic and alkanoic acid chlorides and acid anhydrides. The preferred dehydrating agents are the strong acids, particularly methanesulfonic acid and concentrated sulfuric acid.

Dehydrative cyclizations are run at temperatures from about 20° to about 80°, preferably at room temperature. It is usually preferred to carry out the reactions without solvent, although solvents such as the halogenated benzenes and the halogenated alkanes, including chlorobenzene, the dichlorobenzenes, chloroform and methylene dichloride, may be used if desired.

In another embodiment of the cyclization process, an R-aldehyde, 4-benzoylthiosemicarbazone, of the formula

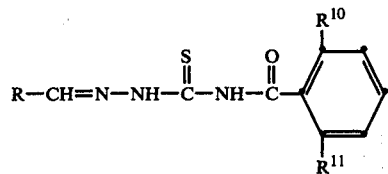

is cyclized in the presence of an oxidizing agent. The preferred oxidizing agent is ferric chloride. Other powerful oxidizing agents can be used, for example, calcium ferricyanide.

Oxidative cyclizations are preferably run in lower alkanols, such as ethanol or propanol, at the reflux temperature of the reaction mixture. In general, however, temperatures from about 50° to about 100° may be used if convenient.

It is preferred to prepare compounds having an amino or acetamido group on a phenyl R group by first preparing the corresponding nitro-substituted compound, and reducing the nitro group by hydrogenation, using a hydrogenation catalyst such as a noble metal catalyst, to form the amino-substituted compound. The amino group is acylated with acetic anhydride or acetyl halide to prepare the acetamido-substituted compound.

As organic chemists will recognize, all of the starting compounds used in preparing the compounds of this invention are obtainable by those of ordinary skill.

The following examples show the preparation of typical compounds. In all of the examples, the compounds were identified by nuclear magnetic resonance analysis, elemental microanalysis, and, in some cases, by infrared analysis and mass spectroscopy.

The following preparations and examples illustrate typical cyclizations with dehydrating agents.

PREPARATION 1

1-(4-chlorobenzoyl)-4-(2,6-dimethoxybenzoyl)thiosemicarbazide

A solution of 0.76 g. of ammonia thiocyanate in 20 ml. of chlorobenzene was heated to 70° in a 100 ml. flask. After a few minutes, 2.0 g. of 2,6-dimethoxybenzoyl chloride in 30 ml. of chlorobenzene was added dropwise, and the mixture was stirred for 15 minutes after the addition was complete. Then, 1.7 g. of 4-chlorobenzoylhydrazine suspended in 20 ml. of chlorobenzene was added, and the resulting mixture was stirred at 70° for 30 minutes. The solvent was then removed under vacuum, and 50 ml. of water was added to the residue. After the aqueous mixture had been stirred for about 3 hours, the solids were collected and dried to obtain 2.7 g. of 1-(4-chlorobenzoyl)-4-(2,6-dimethoxybenzoyl)thiosemicarbazide, m.p. 206°-208°.

|   | Theoretical | Found  |
|---|-------------|--------|
| C | 51.84%      | 52.12% |
| H | 4.09        | 4.35   |
| N | 10.67       | 10.67  |

EXAMPLE 1

N-[5-(4-chlorophenyl)-1,3,4-thiadiazol-2-yl]-2,6-dimethoxybenzamide

A 1 g. portion of the above intermediate was added slowly, with stirring and cooling, to 5 g. of concentrated sulfuric acid. The mixture was stirred at room temperature for 4 hours, and was then poured into 300 ml. of ice. The solids which precipitated were collected, dried and recrystallized from ethyl acetate to produce 0.45 g. of N-[5-(4-chlorophenyl)-1,3,4-thiadiazol-2-yl]-2,6-dimethoxybenzamide, m.p. 238°-240° C.

|   | Theoretical | Found  |
|---|-------------|--------|
| C | 54.33%      | 54.01% |
| H | 3.75        | 3.84   |
| N | 11.18       | 11.22  |

PREPARATION 2

1-(4-hydroxybenzoyl)-4-(2,6-dimethoxybenzoyl)thiosemicarbazide

A 2.0 g. portion of 2,6-dimethoxybenzoyl chloride was dissolved in 20 ml. of tetrahydrofuran, and was added to 0.76 g. of ammonium thiocyanate in 10 ml. of tetrahydrofuran at the reflux temperature. After the addition was complete, the mixture was stirred at reflux temperature for 15 minutes, and then 1.5 g. of 4-hydroxybenzoylhydrazine in 20 ml. of tetrahydrofuran was added. The reaction mixture was refluxed for 30 minutes more, cooled, and evaporated under vacuum to produce an oily residue which consisted largely of 1-(4-hydroxybenzoyl)-4-(2,6-dimethoxybenzoyl)thiosemicarbazide.

EXAMPLE 2

N-[5-(4-hydroxyphenyl)-1,3,4-thiadiazol-2-yl]-2,6-dimethoxybenzamide

The residue produced above was stirred, and 20 g. of methanesulfonic acid was added dropwise to it. After 4 hours of stirring, at room temperature, the solution was poured into 300 ml. of ice water, and the pH was adjusted with ammonium hydroxide to 7.5. A precipitate separated, which was collected and recrystallized from acetone to produce 2.5 g. of N-[5-(5-hydroxyphenyl)-1,3,4-thiadiazol-2-yl]-2,6-dimethoxybenzamide, m.p. above 260°.

|   | Theoretical | Found |
|---|---|---|
| C | 57.13% | 56.98% |
| H | 4.23 | 3.96 |
| N | 11.76 | 11.52 |

EXAMPLE 3

N-[5-(4-pyridyl)-1,3,4-thiadiazol-2-yl]2,6-dimethoxybenzamide

Following the process of Examples 1 and 2, 2.2 g. of 2,6-dimethoxybenzoyl chloride was reacted with 1.4 g. of 4-pyridylcarbonylhydrazine to prepare the corresponding 1-(4-pyridylcarbonyl)-4-(2,6-dimethoxybenzoyl)thiosemicarbazide.

The thiosemicarbazide, a liquid, was stirred while 20 g. of methanesulfonic acid was added dropwise with cooling. After 5 hours of stirring at room temperature, the reaction mixture was worked up as described above to prepare 2.9 g. of N-[5-(4-pyridyl)-1,3,4-thiadiazol-2-yl]-2,6-dimethoxybenzamide, m.p. 241°–243°.

|   | Theoretical | Found |
|---|---|---|
| C | 56.13% | 55.90% |
| H | 4.12 | 4.21 |
| N | 16.36 | 16.47 |

EXAMPLE 4

N-[5-(5-chloro-2-benzo[b]thienyl)-1,3,4-thiadiazol-2-yl]-2,6-dimethoxybenzamide

A 4 g. portion of 1-[(5-chloro-2-benzo[b]thienyl)-carbonyl]-4-(2,6-dimethoxybenzoyl)thiosemicarbazide, prepared as above, was added to 20 g. of methanesulfonic acid to produce about 1.1 g. of N-[5-(5-chloro-2-benzo[b]thienyl)-1,3,4-thiadiazol-2-yl]-2,6-dimethoxybenzamide, m.p. > 260°.

|   | Theoretical | Found |
|---|---|---|
| C | 52.84% | 52.62% |
| H | 3.27 | 3.48 |
| N | 9.73 | 9.78 |

EXAMPLE 5

N-[5-(2-benzothiazolyl)-1,3,4-thiadiazol-2-yl]-2,6-dimethoxybenzamide

A 4.2 g. portion of 1-[(2-benzothiazolyl)carbonyl]-4-(2,6-dimethoxybenzoyl)thiosemicarbazide was added dropwise with stirring to 16 g. of methanesulfonic acid. The product was 2.6 g. of N-[5-(2-benzothiazolyl-1,3,4-thiadiazol-2-yl]-2,6-dimethoxybenzamide, m.p. > 260°.

|   | Theoretical | Found |
|---|---|---|
| C | 54.26% | 54.38% |
| H | 3.54 | 3.72 |
| N | 14.06 | 13.81 |

EXAMPLE 6

N-[5-(2-chlorophenyl)-1,3,4-thiadiazol-2-yl]-2,6-dimethoxybenzamide

To 10 g. of methanesulfonic acid was added 1.4 g. of 1-(2-chlorobenzoyl)-4-(2,6-dimethoxybenzoyl)thiosemicarbazide while the temperature was held at or below 35°. The product of the reaction was 1.2 g. of N-[5-(2-chlorophenyl)-1,3,4-thiadiazol-2-yl]-2,6-dimethoxybenzamide, m.p. 235°–237°.

|   | Theoretical | Found |
|---|---|---|
| C | 54.33% | 54.57% |
| H | 3.75 | 3.95 |
| N | 11.18 | 11.19 |

EXAMPLE 7

N-[5-(2-quinolyl)-1,3,4-thiadiazol-2-yl]-2,6-dimethoxybenzamide

A 2.0 g. portion of 2,6-dimethoxybenzoyl chloride was reacted with 1.9 g. of (2-quinolyl)carbonylhydrazine to form the corresponding 1-(2-quinolylcarbonyl)-4-(2,6-dimethoxybenzoyl)thiosemicarbazide, which was cyclized with methanesulfonic acid to produce 1.75 g. of N-[5-(2-quinolyl)-1,3,4-thiadiazol-2-yl]-2,6-diomethoxybenzamide, m.p. > 260°.

|   | Theoretical | Found |
|---|---|---|
| C | 61.21% | 61.09% |
| H | 4.11 | 4.30 |
| N | 14.28 | 13.95 |

EXAMPLE 7a

N-[5-(3-quinolyl)-1,3,4-thiadiazol-2-yl]-2,6-dimethoxybenzamide

Following the process described above, 2.0 g. of 2,6-dimethoxybenzoyl chloride was reacted with (3-quinolyl)carbonylhydrazine to form 1-(3-quinolylcarbonyl)-4-(2,6-dimethoxybenzoyl)thiosemicarbazide, which was cyclized with methanesulfonic acid to produce 1.7 g. of N-[5-(3-quinolyl)-1,3,4-thiadiazol-2-yl]-2,6-dimethoybenzamide, m.p. 242°–243°.

|   | Theoretical | Found |
|---|---|---|
| C | 61.22% | 60.97% |
| H | 4.11 | 4.17 |

-continued

|   | Theoretical | Found |
|---|---|---|
| N | 14.28 | 14.01 |

The following preparation illustrates a typical oxidative cyclization with ferric chloride.

PREPARATION 3

2-amino-5-(4-pyridyl)-1,3,4-thiadiazole

A 9.0 g. portion of 4-pyridylaldehyde, thiosemicarbazone, was added to 450 ml. of ethanol and 54 g. of ferric chloride hexahydrate was added. The mixture was stirred at reflux temperature for one hour, and was then cooled and the solvent was removed under vacuum. The residue was mixed with 40 ml. of cold concentrated hydrochloric acid, and the mixture was stored overnight in the freezer. The mixture was then filtered, and the solids were washed with three 15-ml. portions of concentrated hydrochloric acid and were dissolved in water. The pH of the solution was adjusted to 8.0 with sodium hydroxide, and the mixture was filtered again. The solids were washed with ethanol. The wash liquid was then evaporated to dryness, and the resulting residue was recrystallized from acetone. The combined yield was 1.3 g of 2-amino-5-(4-pyridyl)-1,3,4-thiadiazole, m.p. 234°-346°.

|   | Theoretical | Found |
|---|---|---|
| C | 47.18% | 47.02% |
| H | 3.39 | 3.45 |
| N | 31.44 | 31.39 |

The following two preparations illustrate dehydrative cyclizations with methanesulfonic acid and with sulfuric acid.

PREPARATION 4

2-amino-5-(4-chlorophenyl)-1,3,4-thiadiazole

A 50 g. portion of 1-(4-chlorobenzoyl)thiosemicarbazide was slowly added with stirring to 330 g. of methanesulfonic acid, while the temperature was held below 35° C. The mixture was stirred for 5 hours after the addition was complete, and was then poured into a liter of ice water. The pH of the mixture was adjusted to 7.5 with ammonium hydroxide, and the precipitated solids were removed by filtration and dried. The solids were then recrystallized from ethanol. Repeated recrystallizations produced a total of 33.3 g. of 2-amino-5-(4-chlorophenyl)-1,3,4-thiadiazole, which was positively identified by nuclear magnetic resonance analysis.

|   | Theoretical | Found |
|---|---|---|
| C | 45.39% | 45.61% |
| H | 2.86 | 3.12 |
| N | 19.85 | 19.70 |

PREPARATION 5

2-amino-5-(4-chlorophenyl)-1,3,4-thiadiazole

To 48 g. of concentrated sulfuric acid at room temperature was slowly added 4.78 g. of 1-(4-chlorobenzoyl)thiosemicarbazide. The temperature rose approximately 10° during the addition. The mixture was stirred at room temperature for 6 hours after the addition was complete. The reaction mixture was then poured into ice, made basic to pH 7.5 with ammonium hydroxide, and filtered. The dried solids were recrystallized from ethanol to produce 2.4 g. of 2-amino-5-(4-chlorophenyl)-1,3,4-thiadiazole, m.p. 221° C.

|   | Theoretical | Found |
|---|---|---|
| C | 45.39% | 45.28% |
| H | 2.86 | 2.63 |
| N | 19.85 | 20.02 |

The following examples are typical of the acylation of aminothiadiazoles to produce compounds of this invention.

EXAMPLE 8

N-[5-(4-chlorophenyl)-1,3,4-thiadiazol-2-yl]-2,6-dichlorobenzamide

To 4 g. of 2-amino-5-(4-chlorophenyl)-1,3,4-thiadiazole in 200 ml. of tetrahydrofuran at room temperature was added, with cooling and stirring, 1.85 g. of 50 percent sodium hydride in oil. The cooling mantle was then removed, and the reaction mixture was stirred for 15 minutes, after which 4.8 g. of 2,6-dichlorobenzoyl chloride was added dropwise. The mixture was stirred for 1 hour more, and excess sodium hydride was decomposed by the addition of water. The solvent was evaporated, and the residue was suspended in water and acidified with hydrochloric acid. The solids were removed from the acid solution by filtration, dried and recrystallized from ethyl acetate to produce 4 g. of N-[5-(4-chlorophenyl)-1,3,4-thiadiazol-2-yl]-2,6-dichlorobenzamide, m.p. >260° C.

|   | Theoretical | Found |
|---|---|---|
| C | 46.84% | 46.60% |
| H | 2.10 | 1.90 |
| N | 10.92 | 10.75 |

EXAMPLE 8a

N-[5-(3-hydroxyphenyl)-1,3,4-thiadiazol-2-yl]-2,6-dimethoxybenzamide

To 1.9 g. of 2-amino-5-(3-hydroxyphenyl)-1,3,4-thiadiazole in 100 ml. of pyridine was added 2.2 g. of 2,6-dimethoxybenzoyl chloride. The reaction mixture was stirred for three hours, with cooling as necessary to hold the temperature below 30°. The volatile substances were then evaporated under vacuum, and the residue was diluted with water. The aqueous mixture was stirred for 3 hours, and the solids were collected and recrystallized from acetone to produce 1.3 g. of N-[5-(3-hydroxyphenyl)-1,3,4-thiadiazol-2-yl]-2,6-dimethoxybenzamide, m.p. 243°-245°.

|   | Theoretical | Found |
|---|---|---|
| C | 57.13% | 57.38% |
| H | 4.23 | 4.36 |
| N | 11.76 | 12.01 |

Synthesis of the following exemplary compounds followed, in general, the process of Examples 8 and 8a. In each example below, the substituents of the aminothiadiazole and the benzoyl halide are obvious from the name of the product. The exemplary compounds will first be named, and then the amounts of the reactants, and the amounts, melting points and elemental analyses of the products, will be tabulated.

EXAMPLE 9
N-[5-(1-naphthyl)-1,3,4-thiadiazol-2-yl]-2,6-dimethoxybenzamide

EXAMPLE 10
N-[5-(2,4-dichlorophenyl)-1,3,4-thiadiazol-2-yl]-2,6-dimethoxybenzamide

EXAMPLE 11
N-[4-hydroxyphenyl)-1,3,4-thiadiazol-2-yl]-2,6-dimethoxybenzamide

EXAMPLE 12
N-[5-(3,5-dichlorophenyl)-1,3,4-thiadiazol-2-yl]-2,6-dimethoxybenzamide

EXAMPLE 13
N-[5-(3-fluorophenyl)-1,3,4-thiadiazol-2-yl]-2,6-dimethoxybenzamide

EXAMPLE 14
N-[5-(4-pyridyl)-1,3,4-thiadiazol-2-yl]-2,6-dimethoxybenzamide

EXAMPLE 15
N-[5-(4-cyanophenyl)-1,3,4-thiadiazol-2-yl]-2,6-dimethoxybenzamide

EXAMPLE 16
N-[5-[3,5-bis(trifluoromethyl)phenyl]-1,3,4-thiadiazol-2-yl]-2,6-dimethoxybenzamide

EXAMPLE 17
N-[5-(2-fluorophenyl)-1,3,4-thiadiazol-2-yl]-2,6-dimethoxybenzamide

EXAMPLE 18
N-(5-phenyl-1,3,4-thiadiazol-2-yl)-2,6-dichlorobenzamide

EXAMPLE 19
N-[5-(4-trifluoromethylphenyl)-1,3,4-thiadiazol-2-yl]-2,6-dichlorobenzamide

EXAMPLE 20
N-[5-(4-chlorophenyl)-1,3,4-thiadiazol-2-yl]-2-chloro-6-methylbenzamide

EXAMPLE 21
N-[5-(4-chlorophenyl)-1,3,4-thiadiazol-2-yl]-2,6-difluorobenzamide

EXAMPLE 22
N-[5-(4-chlorophenyl)-1,3,4-thiadiazol-2-yl]-2,6-dimethylbenzamine

EXAMPLE 23
N-[5-(4-bromophenyl)-1,3,4-thiadiazol-2-yl]-2,6-dichlorobenzamide

EXAMPLE 24
N-[5-(4-fluorophenyl)-1,3,4-thiadiazol-2-yl]-2,6-dichlorobenzamide

EXAMPLE 25
N-[5-(4-chlorophenyl)-1,3,4-thiadiazol-2-yl]-2,6-dimethoxybenzamide

EXAMPLE 26
N-[5-(3,4-dichlorophenyl)-1,3,4-thiadiazol-2-yl]-2,6-dimethylbenzamide

EXAMPLE 27
N-[5-(4-fluorophenyl)-1,3,4-thiadiazol-2-yl]-2,6-dimethylbenzamide

EXAMPLE 28
N-[5-(4-trifluoromethylphenyl)-1,3,4-thiadiazol-2-yl]-2,6-dimethylbenzamide

EXAMPLE 29
N-[5-(4-bromophenyl)-1,3,4-thiadiazol-2-yl]-2,6-dimethylbenzamide

EXAMPLE 30
N-(5-phenyl-1,3,4-thiadiazol-2-yl)-2,6-dimethylbenzamide

EXAMPLE 31
N-[5-(4-fluorophenyl)-1,3,4-thiadiazol-2-yl]-2,6-dimethoxybenzamide

EXAMPLE 32
N-[5-(2-thienyl)-1,3,4-thiadiazol-2-yl]-2,6-dimethoxybenzamide

EXAMPLE 33
N-[5-(2-furyl)-1,3,4-thiadiazol-2-yl]-2,6-dimethoxybenzamide

EXAMPLE 34
N-[5-(4-methylphenyl)-1,3,4-thiadiazol-2yl]-2,6-dimethoxybenzamide

EXAMPLE 35
N-[5-(4-phenylphenyl)-1,3,4-thiadiazol-2-yl]-2,6-dimethoxybenzamide

EXAMPLE 36
N-[5-(3-trifluoromethylphenyl)-1,3,4-thiadiazol-2-yl]-2,6-dimethoxybenzamide

EXAMPLE 37
N-[5-(3-chlorophenyl)-1,3,4-thiadiazol-2-yl]-2,6-dimethoxybenzamide

EXAMPLE 38
N-[5-(4-trifluoromethylphenyl)-1,3,4-thiadiazol-2-yl]-2,6-dimethoxybenzamide

EXAMPLE 39
N-(5-phenyl-1,3,4-thiadiazol-2-yl)-2,6-dimethoxybenzamide

EXAMPLE 40
N-[5-(4-chlorophenyl)-1,3,4-thiadiazol-2yl]-2-methoxybenzamide

EXAMPLE 41
N-[5-(3-trifluoromethylphenyl)-1,3,4-thiadiazol-2-yl)-2,6-dimethylbenzamide

EXAMPLE 42
N-[5-[4-(4-bromophenyl)phenyl]-1,3,4-thiadiazol-2-yl]-2,6-dimethoxybenzamide

EXAMPLE 43
N-[5-[4-(4-chlorophenyl)phenyl]-1,3,4thiadiazol-2-yl]-2,6-dimethoxybenzamide

EXAMPLE 44
N-[5-(4-bromophenyl)-1,3,4-thiadiazol-2-yl]-2,6-dimethoxybenzamide

EXAMPLE 45
N-[5-[4-(4-fluorophenyl)phenyl]-1,3,4-thiadiazol-2-yl]-2,6-dimethoxybenzamide

EXAMPLE 46
N-[5-(2-naphthyl)-1,3,4-thiadiazol-2-yl]-2,6-dimethoxybenzamide

EXAMPLE 47
N-[5-(3,4-dichlorophenyl)-1,3,4-thiadiazol-2-yl]-2,6-dimethoxybenzamide

EXAMPLE 48
N-[5-(3-hydroxyphenyl-1,3,4-thiadiazol-2-yl]-2,6-dimethoxybenzamide

EXAMPLE 49
N-[5-(4-methoxyphenyl)-1,3,4-thiadiazol-2-yl]-2,6-dimethoxybenzamide

EXAMPLE 50
N-[5-(4-nitrophenyl-1,3,4-thiadiazol-2-yl]-2,6-dimethoxybenzamide

EXAMPLE 51
N-[5-(3-chlorophenyl)-1,3,4-thiadiazol-2-yl]-2,6-dimethylbenzamide

EXAMPLE 52
N-[5-(2-naphthyl)-1,3,4-thiadiazol-2-yl]-2,6-dimethylbenzamide

EXAMPLE 53
N-[5-(3,5-bis(trifluoromethyl)phenyl)-1,3,4-thiadiazol-2-yl]-2,6-dimethylbenzamide

EXAMPLE 54
N-[5-(3-thienyl)-1,3,4-thiadiazol-2-yl]-2,6-dimethoxybenzamide

EXAMPLE 55
N-[5-(3-furyl)-1,3,4-thiadiazol-2-yl]-2,6-dimethoxybenzamide

EXAMPLE 56
N-[5-(5-bromo-2-furyl)-1,3,4-thiadiazol-2-yl]-2,6-dimethoxybenzamide

EXAMPLE 57
N-[5-(4-iodophenyl)-1,3,4-thiadiazol-2-yl]-2,6-dimethoxybenzamide

EXAMPLE 58
N-[5-(5-bromo-3-pyridyl)-1,3,4-thiadiazol-2-yl]-2,6-dimethoxybenzamide

EXAMPLE 59
N-[5-(5-chloro-2-thienyl)-1,3,4-thiadiazol-2-yl]-2,6-dimethoxybenzamide

EXAMPLE 60
N-[5-(3-isoxazoyl)-1,3,4-thiadiazol-2-yl]-2,6-dimethoxybenzamide

EXAMPLE 61 -isoxazolyl)-
N-[5-(6-trifluoromethyl-2-benzo[b]furyl-1,3,4-thiadiazol-2-yl]-2,6-dimethoxybenzamide

EXAMPLE 62
N-[5-(5-fluoro-2-benzo[b]furyl)-1,3,4-thiadiazol-2-yl]-2,6-dimethoxybenzamide

EXAMPLE 63
N-[5-(5-methoxy-2-benzo[b]furyl)-1,3,4-thiadiazol-2-yl]-2,6-dimethoxybenzamide

EXAMPLE 64
N-[5-(6-methoxy-2-benzo[b]furyl)-1,3,4-thiadiazol-2-yl]-2,6-dimethoxybenzamide

EXAMPLE 65
N-[5-(5-chloro-2-benzo[b]furyl)-1,3,4-thiadiazol-2-yl]-2,6-dimethoxybenzamide

EXAMPLE 66
N-[5-(5-trifluoromethyl-2-benzo[b]furyl)-1,3,4-thiadiazol-2-yl]-2,6-dimethoxybenzamide

EXAMPLE 67
N-[5-(2-benzo[b]furyl)-1,3,4-thiadiazol-2-yl]-2,6-dimethoxybenzamide

EXAMPLE 68
N-[5-(2-indenyl)-1,3,4-thiadiazol-2-yl]-2,6-dimethoxybenzamide

EXAMPLE 69
N-[5-(4-pentafluoroethoxyphenyl)-1,3,4-thiadiazol-2yl]-2,6-dimethoxybenzamide

| Example No. | Aminothiadiazole | Benzoyl Chloride | Product | M.P., + C. | %C | %H | %N |
|---|---|---|---|---|---|---|---|
| 9  | 2.3 g. | 2.2 g. | 2.0 g. | 209–210 | 64.24 | 4.58 | 10.88 |
| 10 | 2.5 | 2.2 | 2.3 | >260 | 49.56 | 3.17 | 10.30 |
| 11 | 2.0 | 2.3 | 1.5 | >260 | 57.38 | 4.45 | 11.55 |
| 12 | 2.5 | 2.2 | 2.5 | 249–251 | 49.89 | 3.25 | 10.49 |
| 13 | 2.0 | 2.2 | 2.3 | 216–218 | 57.00 | 4.07 | 11.75 |
| 14 | 1.3 | 1.6 | 1.5 | 241–243 | 55.89 | 4.11 | 16.06 |
| 15 | 2.0 | 2.2 | 1.8 | >260 | 58.82 | 3.85 | 15.09 |
| 16 | 3.2 | 2.2 | 2.1 | 236–237 | 48.01 | 2.81 | 9.07 |
| 17 | 2.0 | 2.2 | 1.6 | 248–249 | 57.12 | 3.74 | 11.77 |
| 18 | 3.5 | 4.5 | 3.0 | 232–237 | 51.22 | 2.59 | 11.99 |
| 19 | 2.3 | 2.4 | 2.3 | >260 | 45.96 | 1.90 | 9.96 |
| 20 | 2.0 | 2.0 | 2.5 | 258–260 | 52.61 | 2.91 | 11.58 |

-continued

| Example No. | Amino-thiadiazole | Benzoyl Chloride | Product | M.P., °C. | %C | %H | %N |
|---|---|---|---|---|---|---|---|
| 21 | 2.0 | 2.0 | 0.8 | >260 | 50.97 | 2.57 | 11.86 |
| 22 | 2.0 | 2.0 | 1.8 | 247–249 | 59.42 | 4.22 | 11.94 |
| 23 | 2.4 | 2.4 | 2.8 | >260 | 42.27 | 2.13 | 9.58 |
| 24 | 2.0 | 2.4 | 1.8 | 254–256 | 47.84 | 4.55 | 11.24 |
| 25 | 2.1 | 2.3 | 2.6 | 238–240 | 54.12 | 4.07 | 11.11 |
| 26 | 2.4 | 2.0 | 1.9 | >260 | 54.35 | 3.66 | 11.16 |
| 27 | 2.0 | 2.0 | 1.7 | 231–233 | 62.16 | 4.52 | 12.70 |
| 28 | 2.3 | 2.0 | 1.9 | 240–242 | 57.19 | 4.04 | 11.30 |
| 29 | 2.4 | 2.0 | 0.5 | 250–252 | 52.23 | 3.80 | 11.11 |
| 30 | 2.7 | 3.0 | 2.8 | 248–250 | 65.72 | 4.77 | 13.28 |
| 31 | 2.0 | 2.3 | 1.9 | 248–251 | 57.11 | 3.95 | 11.53 |
| 32 | 2.0 | 2.4 | 2.6 | 256–259 | 52.06 | 3.92 | 11.74 |
| 33 | 2.0 | 2.6 | 1.6 | 233–235 | 54.39 | 4.12 | 12.52 |
| 34 | 2.6 | 3.1 | 3.1 | 228–230 | 60.63 | 4.77 | 11.66 |
| 35 | 2.5 | 2.3 | 2.4 | 236–239 | 66.02 | 4.92 | 10.39 |
| 36 | 2.7 | 2.9 | 2.8 | 183–185 | 52.59 | 3.43 | 10.49 |
| 37 | 2.5 | 2.9 | 1.3 | 213–214 | 54.60 | 4.02 | 11.38 |
| 38 | 2.4 | 2.2 | 3.0 | 217–220 | 52.56 | 3.37 | 10.37 |
| 39 | 1.8 | 2.2 | 2.0 | 253–255 | 60.09 | 4.77 | 11.99 |
| 40 | 2.1 | 1.9 | 2.3 | 214–216 | 55.40 | 3.63 | 11.91 |
| 41 | 2.4 | 2.0 | 1.8 | >260 | 57.10 | 3.82 | 11.19 |
| 42 | 3.3 | 2.4 | 1.9 | 259–261 | 55.45 | 3.53 | 8.84 |
| 43 | 2.9 | 2.4 | 1.0 | 259–261 | 61.02 | 3.84 | 9.36 |
| 44 | 2.6 | 2.2 | 2.4 | 240–243 | 48.36 | 3.55 | 10.29 |
| 45 | 1.6 | 1.1 | 1.4 | 255–257 | 63.08 | 4.19 | 10.00 |
| 46 | 2.3 | 2.2 | 2.2 | 230–232 | 64.43 | 4.66 | 11.01 |
| 47 | 2.5 | 2.2 | 2.5 | 255–257 | 50.04 | 3.24 | 10.25 |
| 48 | 1.9 | 2.2 | 1.3 | 243–245 | 57.38 | 4.36 | 12.01 |
| 49 | 2.5 | 2.0 | 2.4 | 239–241 | 58.29 | 4.88 | 11.46 |
| 50 | 2.7 | 2.9 | 1.8 | >260 | 53.07 | 3.51 | 14.36 |
| 51 | 2.1 | 1.9 | 2.0 | >260 | 59.24 | 4.27 | 12.17 |
| 52 | 2.3 | 1.9 | 1.3 | 235–237 | 69.91 | 4.95 | 11.43 |
| 53 | 3.1 | 1.8 | 2.0 | 230–232 | 51.16 | 2.68 | 9.36 |
| 54 | 1.8 | 2.2 | 1.6 | >260 | 52.13 | 3.82 | 12.06 |
| 55 | 1.7 | 2.2 | 2.1 | 255–257 | 54.23 | 4.22 | 12.44 |
| 56 | 1.5 | 1.3 | 1.7 | 207–209 | 43.72 | 3.10 | 10.18 |
| 57 | 1.7 | 1.3 | 2.7 | 180–182 | 43.85 | 3.12 | 8.85 |
| 58 | 2.6 | 2.2 | 2.6 | 259–261 | 45.89 | 3.21 | 13.02 |
| 59 | 1.0 | 1.1 | 1.5 | 259–260 | 47.46 | 3.36 | 11.14 |
| 60 | 0.5 | 0.6 | 0.3 | 228–229 | 50.39 | 3.85 | 16.62 |
| 61 | 2.0 | 1.55 | 1.0 | 206–208 | 53.15 | 3.11 | 9.25 |
| 62 | 2.35 | 2.2 | 1.7 | 244–245 | 56.89 | 3.59 | 10.74 |
| 63 | 2.0 | 1.8 | 1.3 | 255–257 | 58.12 | 4.24 | 9.99 |
| 64 | 0.7 | 0.62 | 0.12 | 215–217 | 58.58 | 4.48 | 8.88 |
| 65 | 1.26 | 1.1 | 0.8 | — | 54.80 | 3.27 | 9.89 |
| 66 | 2.8 | 2.2 | 2.5 | 242–245 | 53.51 | 3.28 | 9.53 |
| 67 | 2.17 | 2.2 | 1.6 | 219–221 | 59.92 | 4.14 | 10.83 |
| 68 | 1.0 | 1.05 | 0.2 | 230–232 | 63.06 | 4.50 | 10.82 |
| 69 | 3.1 | 2.2 | 1.7 | 227–229 | 48.23 | 3.16 | 8.62 |

The following examples illustrate the preparation of amino- and acetamido-substituted compounds.

EXAMPLE 70

N-[5-(4-aminophenyl)-1,3,4-thiadiazol-2-yl]-2,6-dimethoxy-benzamide

A 3.6 g. portion of the nitrophenyl compound prepared in Example 50 was hydrogenated in tetrahydrofuran in the presence of 5% palladium on carbon catalyst. After the hydrogenation, the solvent was evaporated to dryness under vacuum, and the residue was recrystallized from ethyl acetate. The catalyst was washed with ethanol and dimethylformamide, and the solvents were evaporated to dryness. The residue was recrystalized from ethyl acetate, and the combined recrystallized products were identified as 1.8 g. of N-[5-(4-aminophenyl)-1,3,4-thiadiazol-2-yl]-2,6-dimethoxybenzamide, m.p. 232°–234°.

| | Theoretical | Found |
|---|---|---|
| C | 57.30% | 56.95% |
| H | 4.49 | 4.67 |
| N | 15.73 | 15.41 |

EXAMPLE 71

N-[5-(4-acetamidophenyl)-1,3,4-thiadiazol-2-yl[-2,6-dimethoxybenzamide

An 0.5 g. portion of the product of Example 61 was dissolved in 20 ml. of pyridine, and 0.2 ml. of acetic anhydride in 5 ml. of tetrahydrofuran was added while the reaction mixture was cooled to hold the temperature below 35°. After the addition, the mixture was stirred for 16 hours at room temperature, and was evaporated to dryness under vacuum. The residue was recrystallized from ethyl acetate to give 0.25 g. of N-[5-(4-acetamidophenyl)-1,3,4-thiadiazol-2-yl]-2,6-dimethoxybenzamide, m.p. 211°–213°.

| | Theoretical | Found |
|---|---|---|
| C | 57.42% | 57.70% |
| H | 4.31 | 4.61 |
| N | 14.10 | 13.80 |

The compounds described above have been thoroughly tested against live insects to determine the range of their insecticidal efficacy. The following tests are typical of the experiments performed and the results obtained.

In many instances, repeated tests at an application rate have been performed, and the results of such tests have been averaged. Blank spaces in the data tables below indicate that no test at the named application rate has been done. Compounds are identified by their example numbers.

TEST 1

Mexican Bean Beetle and Southern Armyworm Test

Each compound to be tested was formulated by dissolving 10 mg. of the compound in 1 ml. of solvent comprising 1:1 anhydrous ethanol:acetone containing 23 g. of Toximul R and 13 g. Toximul S per liter. (Toximuls are trademarks for sulfonate/nonionic blended surfactants produced by Stepan Chemical Co., Northfield, Ill.) Each sample was then dispersed in 9 ml. of water to provide a 1000 ppm. concentration of the test compound. This dispersion was further diluted with additional water to produce lower concentrations, as indicated in the following table. The dispersion was sprayed evenly over ten-day-old bean plants and the plants were set aside until dry.

Leaves were then removed from the plants, and the cut ends of the leaves were wrapped in water-soaked cotton. Two leaves were placed in each 100-mm. plastic petri dish, and 5 second- or third-instar Mexican bean beetle larvae (*Epilachna varivestis*) and 5 second- or third-instar southern armyworm larvae (*Spodoptera eridania*) were placed in each dish. Three replicate dishes were used for each test compound. The dishes were held at about 25° and 51 percent relative humidity for 4 days, and the first evaluation of the insecticidal efficacy was made. Some of the dishes were held in the controlled room for three days more, and another evaluation was made.

Insecticidal efficacy was rated on the following scale, compared to solvent controls and nontreated controls.

0 = no control
1 = 1–7 larvae dead
2 = 8–14 larvae dead
3 = 15 larvae dead

The following table reports the results of testing typical compounds.

Table 1

| Compound of Example No. | Appln. Rate ppm. | Mexican bean beetle | | Southern armyworm | |
|---|---|---|---|---|---|
| | | 4 day | 7 day | 4 day | 7 day |
| 1 | 1000 | 2 | 3 | 3 | 3 |
| | 100 | 2 | 2 | 3 | 3 |
| | 50 | 2 | 2 | 2 | 2 |
| | 25 | 2 | 2 | 1 | 2 |
| | 10 | 1 | 2 | 0 | 1 |
| 2 | 1000 | 1 | 2 | 0 | 0 |
| | 100 | 1 | 2 | 0 | 0 |
| 3 | 1000 | 2 | 3 | 2 | 3 |
| | 100 | 0 | 0 | 0 | 0 |
| 4 | 1000 | 0 | 2 | 0 | 1 |
| 5 | 1000 | 1 | 3 | 1 | 3 |
| | 100 | 0 | 2 | 1 | 1 |
| 6 | 1000 | 1 | 3 | 2 | 1 |
| | 100 | 1 | 2 | 1 | 1 |
| 7 | 1000 | 2 | | 0 | |
| 7a | 1000 | 2 | 3 | 0 | 2 |
| 8 | 1000 | 0 | 1 | 3 | 3 |
| | 100 | 0 | 0 | 1 | 1 |
| 9 | 1000 | 1 | 2 | 2 | 2 |
| | 100 | 0 | 1 | 0 | 1 |
| 10 | 1000 | 1 | 2 | 2 | 2 |
| | 100 | 1 | 1 | 1 | 0 |
| 12 | 1000 | 0 | 0 | 3 | 3 |
| | 100 | 0 | 0 | 2 | 3 |
| | 50 | | | 1 | 2 |
| | 25 | | | 0 | 2 |
| 13 | 1000 | 1 | 2 | 3 | 3 |
| | 100 | 0 | 2 | 2 | 2 |
| 15 | 1000 | 0 | 0 | 2 | 2 |
| | 100 | 0 | 0 | 0 | 0 |

Table 1-continued

| Compound of Example No. | Appln. Rate ppm. | Mexican bean beetle | | Southern armyworm | |
|---|---|---|---|---|---|
| | | 4 day | 7 day | 4 day | 7 day |
| 16 | 1000 | 1 | 1 | 3 | 3 |
| | 100 | 0 | 1 | 3 | 3 |
| | 50 | 1 | 1 | 3 | 3 |
| | 25 | 2 | 2 | 2 | 3 |
| | 10 | 1 | 1 | 2 | 2 |
| | 5 | 0 | 1 | 1 | 2 |
| 17 | 1000 | 2 | 3 | 3 | 2 |
| | 100 | 1 | 2 | 1 | 0 |
| | 50 | 1 | 2 | 0 | 0 |
| | 25 | 1 | 2 | 0 | 0 |
| 18 | 1000 | 0 | 0 | 3 | 2 |
| | 100 | 0 | | 0 | 0 |
| 19 | 1000 | 0 | 0 | 3 | 3 |
| | 100 | 0 | 0 | 1 | 1 |
| 20 | 1000 | 1 | 2 | 3 | 3 |
| | 100 | 1 | 1 | 2 | 2 |
| 21 | 1000 | 0 | 0 | 2 | 2 |
| | 100 | 0 | 0 | 0 | 0 |
| 22 | 1000 | 2 | 2 | 3 | 3 |
| | 100 | 1 | 2 | 2 | 3 |
| | 50 | 2 | 3 | 1 | 2 |
| | 25 | 1 | 2 | 1 | 1 |
| 23 | 1000 | 0 | 0 | 2 | 2 |
| | 100 | 0 | 0 | 0 | 0 |
| 24 | 1000 | 0 | 0 | 3 | 3 |
| | 100 | 0 | 0 | 1 | 1 |
| 26 | 1000 | 1 | 1 | 0 | 3 |
| | 100 | 0 | 0 | 0 | 0 |
| 27 | 1000 | 1 | 2 | 3 | 3 |
| | 100 | 2 | 2 | 2 | 3 |
| | 50 | 2 | 3 | 2 | 2 |
| | 25 | 2 | 3 | 1 | 2 |
| | 20 | 1 | 3 | 1 | 2 |
| | 10 | 1 | 2 | 1 | 1 |
| 28 | 1000 | 2 | 3 | 3 | 3 |
| | 100 | 1 | 2 | 2 | 2 |
| | 50 | 0 | 1 | 1 | 2 |
| | 25 | 0 | 1 | 0 | 1 |
| 29 | 1000 | 2 | 2 | 3 | 3 |
| | 100 | 1 | 2 | 2 | 2 |
| | 50 | 1 | 2 | 1 | 2 |
| | 25 | 1 | 1 | 0 | 0 |
| 30 | 1000 | 1 | 2 | 2 | 3 |
| | 100 | 1 | 2 | 0 | 0 |
| 31 | 1000 | 2 | 3 | 3 | 3 |
| | 100 | 1 | 2 | 3 | 3 |
| | 50 | 1 | 2 | 2 | 2 |
| | 25 | 0 | 2 | 1 | 2 |
| 32 | 1000 | 1 | 0 | 3 | 2 |
| | 100 | 0 | 0 | 0 | 0 |
| 33 | 1000 | 2 | 2 | 2 | 2 |
| | 100 | 1 | 2 | 0 | 1 |
| 34 | 1000 | 1 | 3 | 2 | 2 |
| | 100 | 0 | 2 | 0 | 0 |
| 35 | 1000 | 0 | 0 | 3 | 3 |
| | 100 | 0 | 0 | 2 | 2 |
| 36 | 1000 | 2 | 2 | 3 | 3 |
| | 100 | 2 | 2 | 2 | 3 |
| | 50 | 2 | 2 | 2 | 2 |
| | 25 | 2 | 2 | 2 | 3 |
| | 10 | 1 | 2 | 2 | 2 |
| | 5 | | | 1 | 2 |
| | 2.5 | | | 1 | 1 |
| 37 | 1000 | 2 | 3 | 2 | 3 |
| | 100 | 2 | 2 | 2 | 2 |
| | 50 | | | 1 | 2 |
| | 25 | | | 1 | 1 |
| 38 | 1000 | 2 | 3 | 3 | 3 |
| | 100 | 2 | 2 | 3 | 3 |
| | 50 | 3 | 3 | 3 | 3 |
| | 25 | 3 | 3 | | |
| | 10 | 2 | 3 | | |
| 39 | 1000 | 2 | 3 | 3 | 3 |
| | 100 | 0 | 1 | 0 | 0 |
| 40 | 1000 | 0 | 1 | 3 | 3 |
| | 100 | 0 | 0 | 0 | 0 |
| 41 | 1000 | 2 | 2 | 2 | 2 |
| | 100 | 0 | 0 | 0 | 0 |
| 42 | 1000 | 0 | 0 | 2 | 3 |
| | 100 | 0 | 0 | 0 | 0 |
| 43 | 1000 | 0 | 0 | 3 | 3 |
| | 100 | 0 | 0 | 1 | 2 |
| 44 | 1000 | 0 | 2 | 1 | 3 |
| | 100 | 1 | 2 | 3 | 3 |
| | 50 | 1 | 3 | 1 | 2 |
| | 25 | 1 | 2 | 2 | 2 |
| 45 | 1000 | 0 | 0 | 3 | 3 |
| | 100 | 1 | 1 | 2 | 2 |
| | 50 | 0 | 1 | 2 | 2 |

Table 1-continued

| Compound of Example No. | Appln. Rate ppm. | Mexican bean beetle 4 day | Mexican bean beetle 7 day | Southern armyworm 4 day | Southern armyworm 7 day |
| --- | --- | --- | --- | --- | --- |
|  | 25 | 0 | 1 | 0 | 1 |
| 46 | 1000 | 0 | 1 | 2 | 1 |
|  | 100 | 1 | 1 | 1 | 0 |
| 47 | 1000 | 1 | 1 | 3 | 3 |
|  | 100 | 0 | 0 | 1 | 1 |
| 48 | 1000 | 1 | 2 | 0 | 0 |
|  | 100 | 0 | 0 | 0 | 0 |
| 49 | 1000 | 2 | 0 | 2 | 0 |
|  | 100 | 0 | 0 | 0 | 0 |
| 50 | 1000 | 2 | 0 | 2 | 0 |
|  | 100 | 0 | 0 | 0 | 0 |
| 51 | 1000 | 2 | 0 | 1 | 0 |
|  | 100 | 0 | 0 | 0 | 0 |
| 52 | 1000 | 1 | 0 | 1 | 0 |
|  | 100 | 0 | 0 | 0 | 0 |
| 53 | 1000 | 1 | 2 | 3 | 3 |
|  | 100 | 0 | 0 | 3 | 3 |
| 54 | 1000 | 1 | 3 | 0 | 0 |
|  | 100 | 0 | 0 | 0 | 0 |
| 55 | 1000 | 1 | 1 | 2 | 2 |
|  | 100 | 0 | 0 | 0 | 0 |
| 56 | 1000 | 3 | 3 | 2 | 3 |
|  | 100 | 1 | 2 | 3 | 3 |
| 57 | 1000 | 3 | 3 | 3 | 3 |
|  | 100 | 2 | 3 | 2 | 2 |
|  | 50 | 3 | 2 | 1 | 1 |
|  | 10 | 1 | 2 | 1 | 1 |
| 58 | 1000 | 0 | 1 | 2 | 2 |
|  | 100 | 0 | 0 | 0 | 1 |
| 59 | 1000 | 1 | 1 | 2 | 3 |
|  | 100 | 0 | 0 | 1 | 1 |
| 60 | 1000 | 1 | 3 | 3 |  |
|  | 100 | 0 | 0 | 0 |  |
| 61 | 1000 | 0 | 2 | 3 | 3 |
|  | 100 | 0 | 2 | 2 | 3 |
| 62 | 1000 | 2 | 2 | 3 | 3 |
|  | 100 | 1 | 1 | 3 | 3 |
| 63 | 1000 | 0 | 0 | 0 | 0 |
|  | 100 | 0 | 0 | 0 | 0 |
| 64 | 1000 | 2 | 2 | 2 | 2 |
|  | 100 | 1 | 2 | 1 | 2 |
| 65 | 1000 | 0 | 3 | 3 | 3 |
|  | 100 | 0 | 1 | 3 | 3 |
| 66 | 1000 | 0 | 3 | 3 | 3 |
|  | 100 | 0 | 2 | 3 | 3 |
| 67 | 1000 | 1 | 3 | 3 | 3 |
|  | 100 | 1 | 3 | 2 | 3 |
| 68 | 1000 | 0 | 1 | 3 | 3 |
|  | 100 | 0 | 0 | 2 | 3 |
| 69 | 1000 | 2 | 3 | 3 | 3 |
|  | 100 | 2 | 3 | 3 | 3 |
| 70 | 1000 | 2 | 0 | 0 | 0 |
|  | 100 | 0 | 0 | 0 | 0 |
| 71 | 1000 | 1 | 0 | 1 | 0 |
|  | 100 | 0 | 0 | 0 | 0 |

TEST 2

Mexican Bean Beetle Emergence Test

This test was performed to determine the ability of representative compounds to prevent the emergence of adult Mexican bean beetles from pupae.

The compounds were formulated as described in Test 1 above. Bean plants were treated as described in Test 1, and leaves of the treated plants were used as hosts for third-instar Mexican bean beetle larvae in petri dishes. Three larvae were used in each dish. New leaves were added to the dishes as needed, while the larvae were maintained until they pupated, in about 3–5 days. The pupae were then placed in clean petri dishes. After 7 to 10 days, the number of adult Mexican bean beetles which had emerged were counted, and the percent control of emergence was determined compared to solvent and untreated controls. Various numbers of dishes of larvae were used in different tests; in each instance, all of the dishes were pooled for determination of the percent control.

Table 2

| Compound of Example No. | Concentration ppm. | % Control |
| --- | --- | --- |
| 1 | 100 | 100 |
|  | 50 | 100 |
|  | 25 | 100 |
|  | 10 | 100 |
| 25 | 100 | 100 |
|  | 50 | 100 |
|  | 25 | 100 |
|  | 10 | 100 |
| 27 | 100 | 100 |
|  | 50 | 100 |
|  | 25 | 100 |
|  | 10 | 100 |
| 28 | 100 | 100 |
|  | 50 | 48 |
|  | 25 | 3 |
|  | 10 | 11 |
| 31 | 100 | 100 |
|  | 50 | 100 |
|  | 25 | 100 |
|  | 10 | 100 |
| 36 | 100 | 100 |
|  | 50 | 100 |
|  | 25 | 100 |
|  | 10 | 100 |
| 37 | 100 | 100 |
|  | 50 | 100 |
|  | 25 | 100 |
|  | 10 | 100 |
| 38 | 100 | 93 |
|  | 50 | 50 |
|  | 25 | 65 |
|  | 10 | 50 |

TEST 3

Mexican Bean Beetle Life Cycle Test

This test was performed essentially according to the method of Test 1 above, except that the larvae were in the late third-instar phase. The larvae were examined after three days to determine the larvicidal effect, and adult emergence was determined by counting the number of emerged adults after the larvae had pupated and all of the untreated controls had emerged.

Table 3

| Compound of Example No. | Appln. Rate ppm. | % Control of Larvae | % Control of Emergence |
| --- | --- | --- | --- |
| 8 | 1000 | 60 | 12 |
|  | 100 | 70 | 0 |
|  | 50 | 60 | 0 |
|  | 25 | 50 | 0 |

TEST 4

Mexican Bean Beetle Life Cycle Test

This test was performed according to the method described immediately above, except that the larvae were second-instar, and they were observed three times, at 3, 8 and 21 days after treatment. The first two observations were of larvicidal effect, as the larvae had not yet begun to pupate. The 21-day observation was a count of emergence of adults from the pupae. In each case, the observations are reported below as percent control, compared to control larvae.

Table 4

| Compound of Example No. | Appln. Rate ppm. | Percent Control 3 day | Percent Control 8 day | Percent Control 21 day |
| --- | --- | --- | --- | --- |
| 1 | 1000 | 11 | 100 | 100 |
|  | 100 | 22 | 100 | 100 |

Table 4-continued

| Compound of Example No. | Appln. Rate ppm. | Percent Control 3 day | 8 day | 21 day |
|---|---|---|---|---|
| | 10 | 0 | 60 | 100 |
| | 1 | 0 | 0 | 71 |
| 8 | 1000 | 0 | 20 | 100 |
| 18 | 1000 | 0 | 0 | 42 |
| 19 | 1000 | 0 | 6 | 100 |
| 20 | 1000 | 0 | 100 | 100 |

TEST 5

Black Blowfly Test

This test demonstrated the efficacy of typical compounds against the black blowfly, *Phormia regina*.

Each test compound was formulated by dissolving 4 mg. of it in 0.4 ml. of acetone and mixing it with 40 g. of homogenized beef liver to give 100 ppm. concentration. Lower concentrations of the compounds were provided by using acetone solution containing over appropriate amounts of the compound.

The treated liver was divided between two 250-cc. plastic cups and each portion was infested with ten 2-day-old blowfly larvae. The liver was placed on a layer of wood chips and was covered with more chips. All the cups, including solvent-treated and untreated control cups, were held in a temperature and humidity-controlled room until the larvae pupated. All of the pupae were then removed, placed in clean plastic petri dishes, and held until adult flys emerged from control pupae.

The number of pupae per cup was recorded at the time the pupae were placed in the petri dishes. The number of emerged adults per dish was also recorded, and the percent adult control is presented in the table below.

Table 5

| Compound of Example No. | Appln. Rate ppm. | % Control of Emergence |
|---|---|---|
| 1 | 100 | 100 |
| | 10 | 15 |
| | 1 | 0 |
| 22 | 100 | 0 |
| | 10 | 0 |
| | 1 | 0 |
| 27 | 100 | 45 |
| | 10 | 0 |
| | 1 | 0 |
| 28 | 100 | 25 |
| | 10 | 0 |
| | 1 | 0 |
| 31 | 100 | 100 |
| | 10 | 45 |
| | 1 | 0 |
| 36 | 100 | 20 |
| | 10 | 0 |
| | 1 | 0 |
| 37 | 100 | 10 |
| | 10 | 0 |
| | 1 | 0 |
| 38 | 100 | 25 |
| | 10 | 0 |
| | 1 | 0 |

TEST 6

Greater Wax Moth Larvicide Test

This test was performed to evaluate certain compounds against the greater wax moth, *Galleria mellonella*, a parasite of beehives.

Sufficient compound to give the desired concentration was dissolved in 5 ml. of acetone and mixed with 49 g. of a diet composed of 25 g. of oatmeal cereal for babies, 10.6 ml. of honey, 8.0 ml. of glycerin, 5.3 ml. of water and 0.5 ml. of liquid vitamin supplement. The acetone was allowed to evaporate, and the treated diet was divided between three petri dishes, to each of which was added five second- and third-instar larvae. The dishes were held in the controlled room for seven days, and percent control of the larvae was determined, compared to controls.

Table 6

| Compound of Example No. | Appln. Rate ppm. | % Control |
|---|---|---|
| 1 | 500 | 0 |
| | 100 | 0 |
| | 50 | 0 |
| | 25 | 0 |
| | 12.5 | 0 |
| 22 | 500 | 100 |
| | 100 | 100 |
| | 50 | 100 |
| | 25 | 13 |
| | 12.5 | 0 |
| 27 | 500 | 100 |
| | 100 | 100 |
| | 50 | 0 |
| | 25 | 0 |
| | 12.5 | 0 |
| 28 | 500 | 100 |
| | 100 | 100 |
| | 50 | 86 |
| | 25 | 13 |
| | 12.5 | 0 |
| 31 | 500 | 100 |
| | 100 | 100 |
| | 50 | 13 |
| | 25 | 0 |
| | 12.5 | 0 |
| 36 | 500 | 100 |
| | 100 | 100 |
| | 50 | 0 |
| | 25 | 0 |
| | 20 | 0 |
| | 12.5 | 13 |
| | 10 | 0 |
| | 5 | 0 |
| | 2.5 | 0 |
| 37 | 500 | 0 |
| | 100 | 0 |
| | 50 | 0 |
| | 25 | 0 |
| | 12.5 | 0 |
| 38 | 500 | 100 |
| | 100 | 13 |
| | 50 | 0 |
| | 25 | 0 |
| | 20 | 7 |
| | 12.5 | 0 |
| | 10 | 0 |
| | 5 | 0 |
| | 2.5 | 0 |

TEST 7

Mexican Bean Beetle Sterilization Test

This test was conducted by exposing adult Mexican bean beetles to bean plants treated with dispersions containing 1000 ppm. of a typical compound of this invention. The adult beetles were maintained on the treated plants until the females had laid eggs, and egg clusters containing from 20 to 30 eggs each were collected and incubated. None of the eggs from beetles fed on plants treated with the compound of Example 36 hatched. The compound completely sterilized the beetles which consumed the treated foliage.

TEST 8

Lepidoptera on Field-Grown Broccoli

Compounds of this invention were tested against lepidoptera pests infesting field-grown broccoli. The broccoli plants were transplanted into field plots, and treatment began approximately four weeks after transplanting.

The compounds named in the tables below were formulated as wettable powders, and were dispersed in water in concentrations such as to provide the application rates named below, when the dispersions were sprayed at the rate of about 1000 liters per hectare.

The compounds were applied three times at 7-day intervals, and the insects infesting the plants were counted seven days after the third application.

The insect control obtained from use of the compounds is described in the tables below as percent reduction in the number of insects, compared to the number of insects infesting untreated control plants.

The broccoli crop was infested primarily by two species, *Pieris rapae* and *Trichoplusia ni.* Control of these two species is reported in the tables below, as is the control of all species of lepidoptera as a group.

| Compound of Example No. | Appln. Rate kg./ha. | Percent Control | | |
|---|---|---|---|---|
| | | Imported Cabbageworm *Pieris rapae* | Cabbage Looper *Trichoplusia ni* | Total Lepidoptera |
| 1 | 0.14 | 49 | 24 | 39 |
| | 0.28 | 77 | 38 | 61 |
| | 0.56 | 67 | 45 | 58 |
| | 1.1 | 91 | 52 | 75 |
| 16 | 0.14 | 91 | 72 | 83 |
| | 0.28 | 100 | 31 | 72 |
| | 0.56 | 100 | 66 | 86 |
| | 1.1 | 100 | 79 | 92 |
| 22 | 0.14 | 40 | 0 | 11 |
| | 0.28 | 49 | 52 | 50 |
| | 0.56 | 72 | 17 | 50 |
| | 1.1 | 91 | 45 | 72 |
| 36 | 0.14 | 44 | 17 | 33 |
| | 0.28 | 77 | 59 | 69 |
| | 0.56 | 95 | 24 | 67 |
| | 1.1 | 91 | 59 | 78 |
| 38 | 0.14 | 95 | 72 | 86 |
| | 0.28 | 86 | 52 | 72 |
| | 0.56 | 95 | 72 | 86 |
| | 1.1 | 100 | 31 | 72 |

TEST 9

Imported Cabbageworm on Field-Grown Broccoli

This test was carried out according to the method described in Test 8 above, except that the compounds were applied only twice instead of three times. The only insect which was counted in this test was Pieris rapae.

| Compound of Example No. | Appln. Rate kg./ha. | Percent Control |
|---|---|---|
| 1 | 0.28 | 66 |
| | 0.56 | 81 |
| | 1.1 | 97 |
| | 2.2 | 97 |
| 16 | 0.28 | 97 |
| | 0.56 | 97 |
| | 1.1 | 100 |
| | 2.2 | 100 |
| 22 | 0.28 | 65 |
| | 0.56 | 81 |
| | 1.1 | 94 |
| | 2.2 | 97 |
| 36 | 0.28 | 75 |
| | 0.56 | 88 |
| | 1.1 | 97 |
| | 2.2 | 97 |
| 38 | 0.28 | 97 |
| | 0.56 | 100 |
| | 1.1 | 100 |
| | 2.2 | 100 |

The above illustrative data show the potent insecticidal effect of the compounds of the present invention. Entomologists will understand that the compounds are broadly useful for the control of insects of the various orders which adversely affect mankind and its economic enterprises.

For example, the compounds control Coleoptera such as Mexican bean beetle, boll weevil, corn rootworm, cereal leaf beetle, flea beetles, borers, Colorado potato beetle, grain beetles, alfalfa weevil, carpet beetle, confused flour beetle, powder post beetle, wireworms, rice weevil, rose beetle, plum curculio and white grubs; Diptera, such as house fly, yellow fever mosquito, stable fly, horn fly, blowfly, cabbage maggot and carrot rust fly; Lepidoptera, such as southern armyworm, codling moth, cutworm, clothes moth, Indianmeal moth, leaf rollers, corn earworm, European corn borer, cabbage worm, cabbage looper, cotton bollworm, bagworm, eastern tent caterpillar, sod webworm and fall armyworm; and Orthoptera, such as German cockroach and American cockroach.

The compounds are useful for reducing populations of insects, and are used in a method of reducing an insect population which comprises applying an insecticidally-effective amount of one of the compounds to a substance to be ingested by the insects.

Insects may be caused to ingest a compound of this invention by applying the compound to any substance which they ingest. For example, plant-infesting insects are readily controlled by applying a compound to plant parts which the insects eat, particularly the foliage. Insects which infest and consume textiles, paper, wood products and the like are readily controlled by applying a compound to such products. The compounds can similarly be effectively used to protect stored grain or seeds.

It is notable that the compounds interfere with the formation of successive stages of insects which ingest them. For example, when adult insects ingest the compounds, the adults are grossly unaffected, but lay sterile eggs. When an insect larva consumes a compound, it dies without metamorphosing into the next larval stage. Last-stage larvae which consume a compound pupate, but die in the pupa form.

Entomologists will understand that it is not inferred that use of a compound of this invention in the method of this invention will necessarily result in the extinction of an insect population. In some instances, of course, the whole population will be killed. In other instances, part of the insects will be killed and others will survive treatment with the compound. The portion of the population which will be killed depends upon the species of insect, the particular compound in use, the application rate, the vigor of the insects, the weather and other factors understood by entomologists. Thus, the term "reducing a population of insects" refers to a decrease in the numbers of living insects, which in some but not all instances will amount to the disappearance of the population of treated insects.

The extent of population reduction accomplished by a compound depends, of course, upon the application rate of the compound. At least an insecticidally-effective amount must be used in all cases. The term "insecticially-effective amount" is used to describe an amount which is sufficient to cause a measurable reduction in the treated insect population. Insecticidally-effective amounts are found, in general, in the range from about 1 to about 1000 ppm.

It will be understood that application rates of insecticides are usually measured in terms of the concentration of the insecticide in the dispersion in which it is applied. The application rate is measured in this way because it is most convenient to apply a sufficient amount of the dispersion to cover the foliage, or other substance to be treated, with a thin film of the dispersion. The amount of dispersion applied is thus dependent upon the surface area of the ingestable substance to be treated, and the amount of the compound depends on its concentration in the dispersion.

The dispersions in which the compounds are applied are prepared from typical insecticidal compositions which are, however, novel because of the presence of the novel compounds of this invention. Most widely useful are aqueous dispersions prepared by mixing a small amount of a concentrated insecticidal composition with an appropriate quantity of water to give the desired concentration of the compound. Such concentrated water-dispersible compositions, containing in general from about 5 to about 90 percent of the compound, are usually in the form of emulsifiable concentrates or wettable powders.

Wettable powders comprise an intimate mixture of the active compound in an inert carrier which is a mixture of a fine inert powder and surfactants. The concentration of the active compound is usually from about 10 percent to about 90 percent by weight. The inert powder is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 50 to about 500 g. per liter of liquid, equivalent to from about 5 percent to about 50 percent, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types and concentrations of surfactants used for wettable powders.

It is equally practical, when desirable for any reason, to apply the compound in the form of a solution in an appropriate organic solvent, usually a bland petroleum oil such as the spray oils which are widely used in agricultural chemistry.

Further, the compounds may be applied as compositions in the forms of dusts and aerosol preparations. Dusts comprise a compound in a finely powdered form, dispersed in a powdered inert carrier. The carrier is usually a powdered clay, such as pyrophyllite, bentonite, a volcanic deposit or montmorillonite. Dusts usually contain concentrations of the compound in the range of from about 0.1 percent to about 10 percent.

Aerosol compositions comprise a compound of the invention dissolved or dispersed in an inert carrier which is a pressure-generating propellant mixture and packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

I claim:

1. A compound of the formula

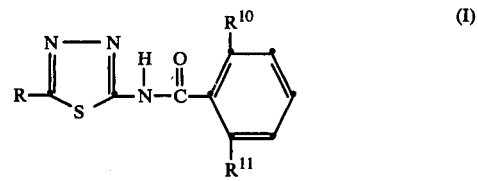

wherein R represents

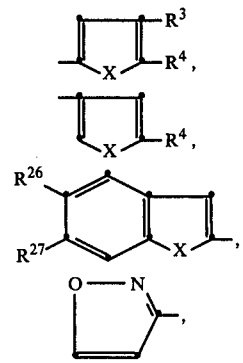

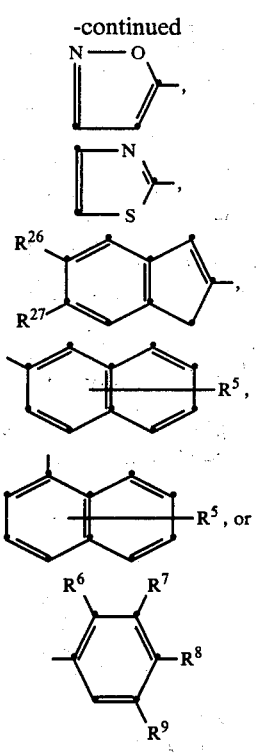

wherein

X represents oxygen or sulfur;

$R^3$ and $R^4$ independently represent hydrogen, chloro, bromo or methyl, provided that $R^3$ represents hydrogen when X represents oxygen;

$R^5$ represents hydrogen, chloro, bromo, fluoro or trifluoromethyl;

one of $R^{26}$ and $R^{27}$ represents hydrogen and the other of $R^{26}$ and $R^{27}$ represents hydrogen, fluoro, chloro, bromo, trifluoromethyl or methoxy;

and either (1) $R^6$ and $R^7$ represent hydrogen, one of $R^8$ and $R^9$ represents hydrogen, and the other of $R^8$ and $R^9$ represents hydrogen, acetamido, chloro, methoxy, bromo, iodo, fluoro, trifluoromethyl, methyl, hydroxy, phenyl, or phenyl monosubstituted with bromo, chloro or fluoro, or (2) $R^6$ and $R^7$ represent hydrogen, and $R^8$ and $R^9$ independently represent chloro, fluoro or bromo, or (3) $R^6$ and $R^8$ represent hydrogen, and $R^7$ and $R^9$ independently represent chloro, fluoro, bromo or trifluoromethyl, or (4) $R^7$ and $R^9$ represent hydrogen, and $R^6$ and $R^8$ independently represent chloro, fluoro or bromo, or (5) $R^7$, $R^8$ and $R^9$ represent hydrogen, and $R^6$ represents chloro, fluoro or bromo, or (6) $R^6$, $R^7$ and $R^9$ represent hydrogen, and $R^8$ represents nitro, amino or cyano, or (7) $R^6$ and $R^7$ represent hydrogen, one of $R^8$ and $R^9$ represents hydrogen and the other of $R^8$ and $R^9$ represents $C_1$-$C_2$ alkoxy substituted with one or more fluorine atoms;

$R^{10}$ and $R^{11}$ independently represent hydrogen, chloro, fluoro, bromo, methyl or methoxy;

provided that:

(1) one of $R^{10}$ and $R^{11}$ may represent hydrogen, if and only if the other represents methoxy;

(2) at least one of $R^{10}$ and $R^{11}$ must represent methyl or methoxy, unless (a) $R^8$ does not represent hydrogen, and $R^6$, $R^7$ and $R^9$ represent hydrogen, or (b) $R^6$ and $R^8$ represent hydrogen, and one or both of $R^7$ and $R^9$ represent trifluoromethyl;

(3) neither $R^8$ nor $R^9$ represents phenyl, acetamido, methoxy, nitro, amino, cyano or substituted phenyl unless both $R^{10}$ and $R^{11}$ represent methoxy;

(4) two of $R^7$, $R^8$ and $R^9$ represent hydrogen unless both $R^{10}$ and $R^{11}$ represent methyl or methoxy;

(5) both $R^{10}$ and $R^{11}$ represent methoxy or methyl when R represents naphthyl, furyl or thienyl;

(6) both $R^{10}$ and $R^{11}$ represent methoxy when R represents benzothienyl, benzofuryl, isoxazolyl or thiazolyl.

2. A compound of claim 1 wherein R represents

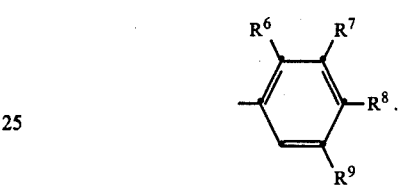

3. A compound of claim 2 wherein $R^{10}$ and $R^{11}$ independently represent methyl or methoxy.

4. A compound of claim 3 wherein one of $R^8$ and $R^9$ represents hydrogen, and the other represents halogen or trifluoromethyl.

5. The compound of claim 4 which is N-[5-(4-chlorophenyl)-1,3,4-thiadiazol-2-yl]-2,6-dimethylbenzamide.

6. The compound of claim 4 which is N-[5-(4-fluorophenyl)-1,3,4-thiadiazol-2-yl]-2,6-dimethylbenzamide.

7. The compound of claim 4 which is N-[5-(4-trifluoromethylphenyl)-1,3,4-thiadiazol-2-yl]-2,6-dimethylbenzamide.

8. A compound of claim 4 wherein $R^{10}$ and $R^{11}$ represent methoxy.

9. The compound of claim 8 which is N-[5-(4-chlorophenyl)-1,3,4-thiadiazol-2-yl]-2,6-dimethoxybenzamide.

10. The compound of claim 8 which is N-[5-(4-fluorophenyl)-1,3,4-thiadiazol-2-yl]-2,6-dimethoxybenzamide.

11. The compound of claim 8 which is N-[5-(3-trifluoromethylphenyl)-1,3,4-thiadiazol-2-yl]-2,6-dimethoxybenzamide.

12. The compound of claim 8 which is N-[5-(3-chlorophenyl)-1,3,4-thiadiazol-2-yl]-2,6-dimethoxybenzamide.

13. The compound of claim 8 which is N-[5-(4-trifluoromethylphenyl)-1,3,4-thiadiazol-2-yl]-2,6-dimethoxybenzamide.

14. A compound of claim 8 wherein $R^7$ and $R^9$ independently represent chloro, fluoro, bromo, or trifluoromethyl.

15. The compound of claim 14 which is N-[5-[3,5-bis(trifluoromethyl)phenyl]-1,3,4-thiadiazol-2-yl]-2,6-dimethoxybenzamide.

16. A compound of claim 3 wherein $R^6$ and $R^7$ represent hydrogen, one of $R^8$ and $R^9$ represents hydrogen and the other of $R^8$ and $R^9$ represents $C_1$-$C_2$ alkoxy substituted with one or more fluorine atoms.

17. The compound of claim 16 which is N-[5-(4-pentafluoroethoxyphenyl)-1,3,4-thiadiazol-2-yl]-2,6-dimethoxybenzamide.

18. A compound of claim 1 of the formula

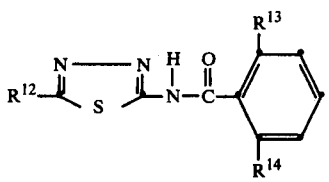

wherein $R^{12}$ represents

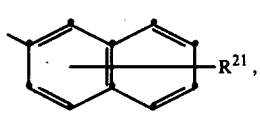

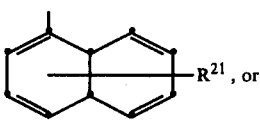, or

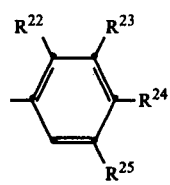

wherein
X represents oxygen or sulfur;
$R^{20}$ represents hydrogen, chloro, bromo or methyl;
$R^{21}$ represents hydrogen, chloro, bromo, fluoro or trifluoromethyl;
and either
(1) $R^{22}$ and $R^{23}$ represent hydrogen, one of $R^{24}$ and $R^{25}$ represents hydrogen, and the other of $R^{24}$ and $R^{25}$ represents hydrogen, chloro, bromo, fluoro, trifluoromethyl, methyl, hydroxy, phenyl, or phenyl monosubstituted with bromo, chloro or fluoro, or
(2) $R^{22}$ and $R^{23}$ represent hydrogen, and $R^{24}$ and $R^{25}$ independently represent chloro, fluoro or bromo, or
(3) $R^{22}$ and $R^{24}$ represent hydrogen, and $R^{23}$ and $R^{25}$ independently represent chloro, fluoro, bromo or trifluoromethyl, or
(4) $R^{23}$ and $R^{25}$ represent hydrogen, and $R^{22}$ and $R^{24}$ independently represent chloro, fluoro or bromo, or
(5) $R^{23}$, $R^{24}$ and $R^{25}$ represent hydrogen, and $R^{22}$ represents chloro, fluoro or bromo, or
(6) $R^{22}$ and $R^{23}$ represent hydrogen, one of $R^{24}$ and $R^{25}$ represents hydrogen and the other of $R^{24}$ and $R^{25}$ represents $C_1$-$C_2$ alkoxy substituted with one or more fluorine atoms;

$R^{13}$ and $R^{14}$ independently represent hydrogen, chloro, fluoro, bromo, methyl or methoxy; provided that:

(1) one of $R^{13}$ and $R^{14}$ may represent hydrogen, if and only if the other represents methoxy;
(2) at least one of $R^{13}$ and $R^{14}$ must represent methyl or methoxy, unless
  a) $R^{24}$ does not represent hydrogen, and $R^{22}$, $R^{23}$, and $R^{25}$ represent hydrogen, or
  b) $R^{22}$ and $R^{24}$ represent hydrogen, and one or both of $R^{23}$ and $R^{25}$ represent trifluoromethyl;
(3) neither $R^{24}$ nor $R^{25}$ represents phenyl or substituted phenyl unless both $R^{13}$ and $R^{14}$ represent methoxy;
(4) two of $R^{23}$, $R^{24}$ and $R^{25}$ represent hydrogen unless both $R^{13}$ and $R^{14}$ represent methyl or methoxy;
(5) both $R^{13}$ and $R^{14}$ represent methoxy when $R^{12}$ represents naphthyl, furyl or thienyl.

19. A compound of claim 18 wherein $R^{12}$ represents

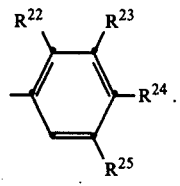

20. A compound of claim 19 wherein both $R^{13}$ and $R^{14}$ represent methoxy.

21. An insecticidal composition which comprises an insecticidally-effective amount of a compound of claim 1 and an inert carrier.

22. A composition of claim 21 wherein the concentration of the compound is from about 0.1 to about 90 percent.

23. A composition of claim 22 wherein the compound is a compound wherein R represents

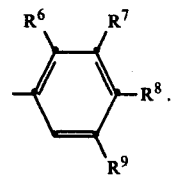

24. A composition of claim 23 wherein the compound is a compound wherein $R^{10}$ and $R^{11}$ independently represent methyl or methoxy.

25. A composition of claim 24 wherein the compound is a compound wherein one of $R^8$ and $R^9$ represents hydrogen, and the other represents halogen or trifluoromethyl.

26. The composition of claim 25 wherein the compound is N-[5-(4-chlorophenyl)-1,3,4-thiadiazol-2-yl]-2,6-dimethylbenzamide.

27. The composition of claim 25 wherein the compound is N-[5-(4-fluorophenyl)-1,3,4-thiadiazol-2-yl]-2,6-dimethylbenzamide.

28. The composition of claim 25 wherein the compound is N-[5-(4-trifluoromethylphenyl)-1,3,4-thiadiazol-2-yl]-2,6-dimethylbenzamide.

29. A composition of claim 25 wherein the compound is a compound wherein $R^{10}$ and $R^{11}$ represent methoxy.

30. The composition of claim 29 wherein the compound is N-[5-(4-chlorophenyl)-1,3,4-thiadiazol-2-yl]-2,6-dimethoxybenzamide.

31. The composition of claim 29 wherein the compound is N-[5-(4-fluorophenyl)-1,3,4-thiadiazol-2-yl]2,6-dimethoxybenzamide.

32. The composition of claim 29 wherein the compound is N-[5-(3-trifluoromethylphenyl)-1,3,4-thiadiazol-2-yl]-2,6-dimethoxybenzamide.

33. The composition of claim 29 wherein the compound is N-[5-(3-chlorophenyl)-1,3,4-thiadiazol-2-yl]-2,6-dimethoxybenzamide.

34. The composition of claim 29 wherein the compound is N-[5-(4-trifluoromethylphenyl)-1,3,4-thiadiazol-2-yl]-2,6-dimethoxybenzamide.

35. A composition of claim 29 wherein the compound is a compound wherein $R^7$ and $R^9$ independently represent chloro, fluoro, bromo, or trifluoromethyl.

36. The composition of claim 35 wherein the compound is N-[5-[3,5-bis(trifluoromethyl)phenyl]-1,3,4-thiadiazol-2-yl]-2,6-dimethoxybenzamide.

37. A composition of claim 24 wherein the compound is a compound wherein $R^6$ and $R^7$ represent hydrogen, one of $R^8$ and $R^9$ represents hydrogen and the other of $R^8$ and $R^9$ represents $C_1$-$C_2$ alkoxy substituted with one or more fluorine atoms.

38. The composition of claim 37 wherein the compound is N-[5-(4-pentafluoroethoxyphenyl)-1,3,4-thiadiazol-2-yl]-2,6-dimethoxybenzamide.

39. An insecticidal composition of claim 22 wherein the compound is of the formula

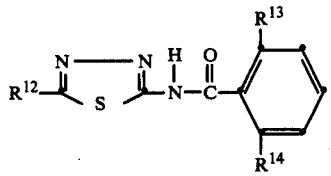

wherein $R^{12}$ represents

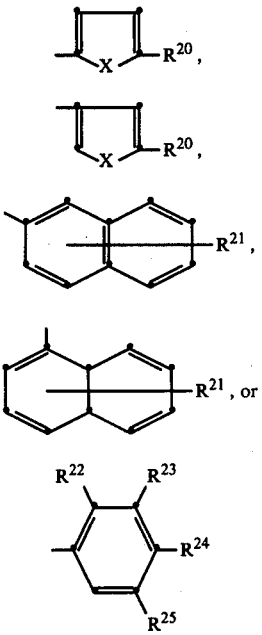

wherein
X represents oxygen or sulfur;
$R^{20}$ represents hydrogen, chloro, bromo or methyl;
$R^{21}$ represents hydrogen, chloro, bromo, fluoro or trifluoromethyl; and either
(1) $R^{22}$ and $R^{23}$ represent hydrogen, one of $R^{24}$ and $R^{25}$ represents hydrogen, and the other of $R^{24}$ and $R^{25}$ represents hydrogen, chloro, bromo, fluoro, trifluoromethyl, methyl, hydroxy, phenyl, or phenyl monosubstituted with bromo, chloro or fluoro, or (2) $R^{22}$ and $R^{23}$ represent hydrogen, and $R^{24}$ and $R^{25}$ independently represent chloro, fluoro or bromo, or (3) $R^{22}$ and $R^{24}$ represent hydrogen, and $R^{23}$ and $R^{25}$ independently represent chloro, fluoro, bromo or trifluoromethyl, or (4) $R^{23}$ and $R^{25}$ represent hydrogen, and $R^{22}$ and $R^{24}$ independently represent chloro, fluoro or bromo, or (5) $R^{23}$, $R^{24}$ and $R^{25}$ represent hydrogen, and $R^{22}$ represents chloro, fluoro or bromo, or (6) $R^{22}$ and $R^{23}$ represent hydrogen, one of $R^{24}$ and $R^{25}$ represents hydrogen and the other of $R^{24}$ and $R^{25}$ represents $C_1$-$C_2$ alkoxy substituted with one or more fluorine atoms;

$R^{13}$ and $R^{14}$ independently represent hydrogen, chloro, fluoro, bromo, methyl or methoxy; provided that:
(1) one of $R^{13}$ and $R^{14}$ may represent hydrogen, if and only if the other represents methoxy;
(2) at least one of $R^{13}$ and $R^{14}$ must represent methyl or methoxy, unless a) $R^{24}$ does not represent hydrogen, and $R^{22}$, $R^{23}$ and $R^{25}$ represent hydrogen or b) $R^{22}$ and $R^{24}$ represent hydrogen, and one or both of $R^{23}$ and $R^{25}$ represent trifluoromethyl;
(3) neither $R^{24}$ nor $R^{25}$ represents phenyl or substituted phenyl unless both $R^{13}$ and $R^{14}$ represent methoxy;
(4) two of $R^{23}$, $R^{24}$ and $R^{25}$ represent hydrogen unless both $R^{13}$ and $R^{14}$ represent methyl or methoxy;
(5) both $R^{13}$ and $R^{14}$ represent methoxy when $R^{12}$ represents naphthyl, furyl or thienyl.

40. A composition of claim 39 wherein the compound is a compound wherein $R^{12}$ represents

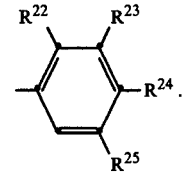

41. A composition of claim 40 wherein the compound is a compound wherein both $R^{13}$ and $R^{14}$ represent methoxy.

42. A method of reducing an insect population which comprises applying an insecticidally-effective amount of a compound of claim 1 to a substance to be ingested by the insects.

43. A method of claim 42 wherein the amount of the compound is from about 1 to about 1000 ppm.

44. A method of claim 43 wherein the compound is a compound wherein R represents

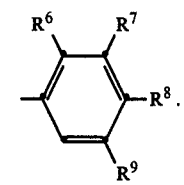

45. A method of claim 44 wherein the compound is a compound wherein $R^{10}$ and $R^{11}$ independently represent methyl or methoxy.

46. A method of claim 45 wherein the compound is a compound wherein one of $R^8$ and $R^9$ represents hydrogen, and the other represents halogen or trifluoromethyl.

47. The method of claim 46 wherein the compound is N-[5-(4-chlorophenyl)-1,3,4-thiadiazol-2-yl]-2,6-dimethylbenzamide.

48. The method of claim 46 wherein the compound is N-[5-(4-fluorophenyl)-1,3,4-thiadiazol-2-yl]-2,6-dimethylbenzamide.

49. The method of claim 46 wherein the compound is N-[5-(4-trifluoromethylphenyl)-1,3,4-thiadiazol-2-yl]-2,6-dimethylbenzamide.

50. A method of claim 46 wherein the compound is a compound wherein $R^{10}$ and $R^{11}$ represent methoxy.

51. The method of claim 50 wherein the compound is N-[5-(4-chlorophenyl)-1,3,4-thiadiazol-2-yl]-2,6-dimethoxybenzamide.

52. The method of claim 50 wherein the compound is N-[5-(4-fluorophenyl)-1,3,4-thiadiazol-2-yl]-2,6-dimethoxybenzamide.

53. The method of claim 50 wherein the compound is N-[5-(3-trifluoromethylphenyl)-1,3,4-thiadiazol-2-yl]-2,6-dimethoxybenzamide.

54. The method of claim 50 wherein the compound is N-[5-(3-chlorophenyl)-1,3,4-thiadiazol-2-yl]-2,6-dimethoxybenzamide.

55. The method of claim 50 wherein the compound is N-[5-(4-trifluoromethylphenyl)-1,3,4-thiadiazol-2-yl]-2,6-dimethoxybenzamide.

56. A method of claim 50 wherein the compound is a compound wherein $R^7$ and $R^9$ independently represent chloro, fluoro, bromo, or trifluoromethyl.

57. The method of claim 56 wherein the compound is N-[5-(3,5-bis(trifluoromethyl)phenyl]-1,3,4-thiadiazol-2-yl]-2,6-dimethoxybenzamide.

58. A method of claim 45 wherein the compound is a compound wherein $R^6$ and $R^7$ represent hydrogen, one of $R^8$ and $R^9$ represents hydrogen and the other of $R^8$ and $R^9$ represents $C_1$–$C_2$ alkoxy substituted with one or more fluorine atoms.

59. The method of claim 58 wherein the compound is N-[5-(4-pentafluoroethoxyphenyl)-1,3,4-thiadiazol-2-yl]-2,6-dimethoxybenzamide.

60. An insecticidal method of claim 43 wherein the compound is of the formula

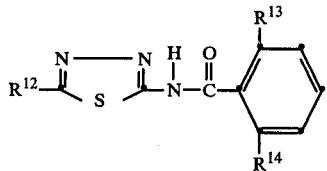

wherein $R^{12}$ represents

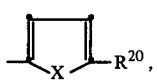

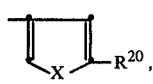

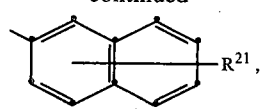

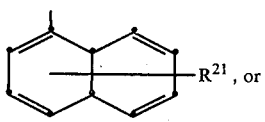

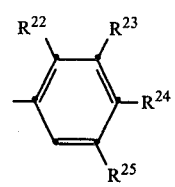

wherein

X represents oxygen or sulfur;

$R^{20}$ represents hydrogen, chloro, bromo or methyl;

$R^{21}$ represents hydrogen, chloro, bromo, fluoro or trifluoromethyl; and either (1) $R^{22}$ and $R^{23}$ represent hydrogen, one of $R^{24}$ and $R^{25}$ represents hydrogen, and the other of $R^{24}$ and $R^{25}$ represents hydrogen, chloro, bromo, fluoro, trifluoromethyl, methyl, hydroxy, phenyl, or phenyl monosubstituted with bromo, chloro or fluoro or (2) $R^{22}$ and $R^{23}$ represent hydrogen, and $R^{24}$ and $R^{25}$ independently represent chloro, fluoro and bromo, or (3) $R^{22}$ and $R^{24}$ represent hydrogen, and $R^{23}$ and $R^{25}$ independently represent chloro, fluoro, bromo or trifluoromethyl, or (4) $R^{23}$ and $R^{25}$ represent hydrogen, and $R^{22}$ and $R^{24}$ independently represent chloro, fluoro or bromo, or (5) $R^{23}$, $R^{24}$ and $R^{25}$ represent hydrogen, and $R^{22}$ represents chloro, fluoro or bromo, or (6) $R^{22}$ and $R^{23}$ represent hydrogen, one of $R^{24}$ and $R^{25}$ represents hydrogen and the other of $R^{24}$ and $R^{25}$ represents $C_1$–$C_2$ alkoxy substituted with one or more fluorine atoms;

$R^{13}$ and $R^{14}$ independently represent hydrogen, chloro, fluoro, bromo, methyl or methoxy; provided that:

(1) one of $R^{13}$ and $R^{14}$ may represent hydrogen, if and only if the other represents methoxy;

(2) at least one of $R^{13}$ and $R^{14}$ must represent methyl or methoxy, unless
  (a) $R^{24}$ does not represent hydrogen, and $R^{22}$, $R^{23}$ and $R^{25}$ represent hydrogen, or
  (b) $R^{22}$ and $R^{24}$ represent hydrogen, and one or both of $R^{23}$ and $R^{25}$ represent trifluoromethyl;

(3) neither $R^{24}$ nor $R^{25}$ represents phenyl or substituted phenyl unless both $R^{13}$ and $R^{14}$ represent methoxy;

(4) two of $R^{23}$, $R^{24}$ and $R^{25}$ represent hydrogen unless both $R^{13}$ and $R^{14}$ represent methyl or methoxy;

(5) both $R^{13}$ and $R^{14}$ represent methoxy when $R^{12}$ represents naphthyl, furyl or thienyl.

61. A method of claim 60 wherein the compound is a compound wherein $R^{12}$ represents

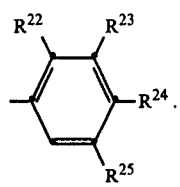
62. A method of claim 61 wherein the compound is a compound wherein both $R^{13}$ and $R^{14}$ represent methoxy.
* * * * *